(12) United States Patent
Cook

(10) Patent No.: US 10,689,589 B2
(45) Date of Patent: Jun. 23, 2020

(54) CYCLIC QUATERNARY AMMONIUM SALTS AS FUEL OR LUBRICANT ADDITIVES

(71) Applicant: INNOSPEC LIMITED, Cheshire (GB)

(72) Inventor: Stephen Leonard Cook, Chester (GB)

(73) Assignee: Innospec Limited, Cheshire (GB)

( * ) Notice: Subject to any disclaimer, the term of this patent is extended or adjusted under 35 U.S.C. 154(b) by 132 days.

(21) Appl. No.: 15/747,950

(22) PCT Filed: Jul. 28, 2016

(86) PCT No.: PCT/GB2016/052312
§ 371 (c)(1),
(2) Date: Jan. 26, 2018

(87) PCT Pub. No.: WO2017/017454
PCT Pub. Date: Feb. 2, 2017

(65) Prior Publication Data
US 2018/0223203 A1 Aug. 9, 2018

(30) Foreign Application Priority Data
Jul. 28, 2015 (GB) .................................. 1513304.4

(51) Int. Cl.
| | | |
|---|---|---|
| *C10L 1/232* | (2006.01) |
| *C10L 10/04* | (2006.01) |
| *C10L 10/06* | (2006.01) |
| *C10M 133/44* | (2006.01) |
| *C10M 133/48* | (2006.01) |
| *C07D 249/02* | (2006.01) |
| *C10L 1/14* | (2006.01) |
| *C07D 207/04* | (2006.01) |
| *C07D 233/58* | (2006.01) |
| *C10L 1/222* | (2006.01) |
| *C10L 1/188* | (2006.01) |
| *C10L 1/19* | (2006.01) |
| *C10L 1/224* | (2006.01) |
| *C10L 1/226* | (2006.01) |
| *C10L 1/2383* | (2006.01) |
| *C10L 1/233* | (2006.01) |
| *C10L 1/238* | (2006.01) |

(52) U.S. Cl.
CPC ............ *C10L 1/232* (2013.01); *C07D 207/04* (2013.01); *C07D 233/58* (2013.01); *C07D 249/02* (2013.01); *C10L 1/14* (2013.01); *C10L 10/04* (2013.01); *C10L 10/06* (2013.01); *C10M 133/44* (2013.01); *C10M 133/48* (2013.01); *C10L 1/188* (2013.01); *C10L 1/1883* (2013.01); *C10L 1/19* (2013.01); *C10L 1/224* (2013.01); *C10L 1/226* (2013.01); *C10L 1/2222* (2013.01); *C10L 1/2225* (2013.01); *C10L 1/233* (2013.01); *C10L 1/238* (2013.01); *C10L 1/2383* (2013.01); *C10L 2200/0423* (2013.01); *C10L 2200/0446* (2013.01); *C10L 2270/023* (2013.01); *C10L 2270/026* (2013.01); *C10M 2215/223* (2013.01); *C10M 2215/224* (2013.01)

(58) Field of Classification Search
CPC combination set(s) only.
See application file for complete search history.

(56) References Cited

U.S. PATENT DOCUMENTS

| | | |
|---|---|---|
| 3,275,554 A | 9/1966 | Wagenaar |
| 3,438,757 A | 4/1969 | Honnen et al. |
| 3,454,555 A | 7/1969 | van der Voort et al. |
| 3,565,804 A | 2/1971 | Honnen et al. |
| 3,755,433 A | 8/1973 | Miller et al. |
| 3,822,209 A | 7/1974 | Knapp et al. |
| 4,171,959 A | 10/1979 | Vartanian |
| 4,288,612 A | 9/1981 | Lewis et al. |
| 5,089,029 A | 2/1992 | Hashimoto et al. |
| 5,112,364 A | 5/1992 | Rath et al. |
| 5,925,151 A | 7/1999 | DeCanio et al. |
| 6,217,624 B1 | 4/2001 | Morris et al. |
| 7,951,211 B2 | 5/2011 | Barton et al. |
| 2008/0052985 A1 | 3/2008 | Stevenson et al. |
| 2008/0060259 A1 | 3/2008 | Breakspear |
| 2008/0060608 A1 | 3/2008 | Breakspear |

(Continued)

FOREIGN PATENT DOCUMENTS

| | | |
|---|---|---|
| EP | 0281994 A1 | 9/1988 |
| EP | 0291074 A2 | 11/1988 |

(Continued)

OTHER PUBLICATIONS

International Preliminary Report on Patentability for International Application No. PCT/GB2016/052312 dated Jan. 30, 2018.
Grellier M., et al., "Allyl versus aryl C—H activation mediated by palladium acetate", Journal of Organometallic Chemistry, vol. 548, No. 2, 1997, pp. 301-304.
Tayeb Belhocine et al., "New Ionic Liquids from Azepane and 3-Methyl piperidine Exhibiting Wide Electrochemical Windows", Green Chemistry, [Online] vol. 13, No. 1, 2011, pp. 59-63.
Rafa Roszak et al: "Effect of chiral ionic liquids on palladium-catalyzed Heckarylation of 2,3-di hydrofuran", Applied Catalysis A : General, vol. 409, 2011, pp. 148-155.

(Continued)

*Primary Examiner* — Ellen M Mcavoy
*Assistant Examiner* — Chantel L Graham
(74) *Attorney, Agent, or Firm* — Burns & Levinson LLP; Janine M. Susan

(57) ABSTRACT

Quaternary ammonium salts of formula: wherein each of $R^1$ and $R^2$ is independently selected from an optionally substituted alkyl, alkenyl or aryl group having less than 8 carbon atoms, R together with N forms an aliphatic or aromatic heterocycle having less than 12 carbons atoms and $R^5$ is hydrogen or an optionally substituted hydrocarbyl group. The use of these compounds as fuel or lubricant additives, especially as diesel fuel additives.

26 Claims, No Drawings

(56) References Cited

U.S. PATENT DOCUMENTS

| | | | |
|---|---|---|---|
| 2008/0113890 A1 | 5/2008 | Moreton et al. | |
| 2008/0269477 A1 | 10/2008 | Stegmann | |
| 2008/0307698 A1 | 12/2008 | Barton et al. | |
| 2009/0253905 A1 | 10/2009 | Ignatyev | |
| 2009/0282731 A1 | 11/2009 | Malfer et al. | |
| 2011/0258917 A1 | 10/2011 | Garcia Castro et al. | |
| 2011/0315107 A1 | 12/2011 | Grabarse et al. | |
| 2012/0010112 A1 | 1/2012 | Grabarse et al. | |
| 2013/0031827 A1 | 2/2013 | Reid et al. | |
| 2013/0205654 A1 | 8/2013 | Peretolchin | |
| 2014/0123547 A1 | 5/2014 | Walter | |
| 2016/0152910 A1* | 6/2016 | Reid | F02M 25/14 123/1 A |

FOREIGN PATENT DOCUMENTS

| | | |
|---|---|---|
| EP | 0565285 B1 | 5/1997 |
| EP | 1254889 A1 | 11/2002 |
| EP | 1884556 A2 | 2/2008 |
| EP | 1900795 A1 | 3/2008 |
| EP | 2940010 A1 | 4/2015 |
| WO | 2006135881 A2 | 12/2006 |
| WO | 2008152003 A1 | 12/2008 |
| WO | 2009040582 A1 | 4/2009 |
| WO | 2009040583 A1 | 4/2009 |
| WO | 2010117836 A1 | 10/2010 |
| WO | 2011095819 A1 | 8/2011 |
| WO | 2011141731 A1 | 11/2011 |
| WO | 2013017889 A1 | 2/2013 |
| WO | 2014064151 A1 | 1/2014 |
| WO | 2014064151 A1 | 5/2014 |
| WO | 2015011507 A1 | 1/2015 |

OTHER PUBLICATIONS

Benlian Lu et al: "Cation does matter: how cationic structure affects the dissolution of cellulose in ionic liquids", Green Chemistry, vol. 16, No. 3, 2014, pp. 1326-1335.

Ann E Rouch et al., "Tartrate-based ionic liquids: unified synthesis and characterization", RSC Advances : An International Journal to Further the Chemical Sciences, vol. 3, No. 2, 2013, pp. 413-426.

International Search Report issued in International Application No. PCT/GB2016/052312 dated Sep. 5, 2016.

Mary Grellier et al., "Allyl versus aryl C—H activation mediated by palladium acetate" Journal of Organometllic Chemistry 548:2, (1997) 301-304.

Tayeb Belhocine et al., "New ionic liquids from azepane and 3-methylpiperidine exhibiting wide electrochemical windows" Green Chemistry, (2011), 13:1, 59-63.

R Roszak et al., "Effect of chiral ionic liquids on palladium-catalyzed Heck arylation of 2,3-dihydrofuran" Applied Catalysis A: General 409 (2011) 148-155.

Benlian Lu et al., "Cation does matter: how cationic structure affects the dissolution of cellulose in ionic liquids" Green Chemistry, (2014), 16:3,-1335.

Anne Rouch et al., "Tartrate-based ionic liquids: unified synthesis and characterisation" RSC Advances: An International Journal to Further the Chemical Sciences, (2013), 3:2, 413-426.

International Search Report and Written Opinion for international application No. PCT/GB2016/052312, filed on Jul. 28, 2016.

UK Search Report (on the priority application) for GB Application No. 1513304.4, filed on Jul. 28, 2015.

* cited by examiner

CYCLIC QUATERNARY AMMONIUM SALTS AS FUEL OR LUBRICANT ADDITIVES

CROSS-REFERENCE TO RELATED APPLICATIONS

This application is a U.S. national stage application under 35 U.S.C. 371 of co-pending International Application No. PCT/GB2016/052312 filed on Jul. 28, 2016, which in turn claims priority to GB Application No. 1513304.4 filed on Jul. 28, 2015, the contents of which are incorporated by reference herein in their entireties for all purposes.

The present invention relates to novel quaternary ammonium compounds, to a composition comprising such compounds and to methods and uses relating thereto.

In particular the present invention relates to the use of quaternary ammonium compounds as fuel or lubricant additives, especially as fuel additives and preferably as diesel fuel additives.

It is common to include nitrogen-containing detergent compounds in lubricating oil and fuel oil compositions in order to improve the performance of engines using such compositions. The inclusion of detergent additives prevents the fouling of moving parts of the engine. Without such additives fouling would cause the performance of the engine to diminish and eventually cease.

Many different types of quaternary ammonium salts are known in the art for use as detergent additives in fuel and lubricating oil compositions. Examples of such compounds are described in U.S. Pat. Nos. 4,171,959 and 7,951,211. One commonly used class of quaternary ammonium additives is prepared by the reaction of a tertiary amine with an epoxide and an acid. These compounds typically include a quaternised nitrogen atom including at least one hydrophobic group. The hydrophobic group is usually a hydrocarbyl chain having at least 8 carbon atoms. The most commonly used quaternary ammonium salt additives are based on compounds having a hydrocarbyl substantive with a molecular weight of at least 200 and typically at least 500. Indeed many of these compounds include a polyisobutenyl substituent having an average molecular weight of 1000 and sometimes higher.

The present inventors have surprisingly found that good deposit control can be achieved when using quaternary ammonium salt additives prepared from cyclic low molecular weight amines.

According to a first aspect of the present invention there is provided a quaternary ammonium salt of formula:

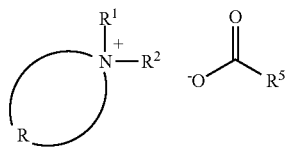

wherein each of $R^1$ and $R^2$ is independently selected from an optionally substituted alkyl, alkenyl or aryl group having less than 8 carbon atoms, R together with N forms an aliphatic or aromatic heterocycle having less than 12 carbon atoms and $R^5$ is hydrogen or an optionally substituted hydrocarbyl group.

The quaternary ammonium salts of the present invention include cations of formula R══N$^+$R$^1$R$^2$, wherein each of $R^1$ and $R^2$ is independently an optionally substituted alkyl, alkenyl or aryl group having less than 8 carbon atoms, and R together with N forms a heterocycle having less than 12 carbon atoms.

For the avoidance of doubt, the structure R══N$^+$R$^1$R$^2$ is used to indicate that the group R forms 2 bonds to N, not that it forms a double bond.

In this specification, unless otherwise stated references to optionally substituted alkyl groups may include aryl-substituted alkyl groups and references to optionally-substituted aryl groups may include alkyl-substituted or alkenyl-substituted aryl groups.

$R^1$ and $R^2$ may be the same or different. In some embodiments they are the same. In some embodiments they are different.

Preferably $R^1$ is an optionally substituted alkyl, alkenyl or aryl group having from 1 to 7 carbon atoms, preferably from 1 to 5 carbon atoms, more preferably from 1 to 4 carbon atoms.

$R^1$ may be optionally substituted with one or more groups selected from halo (especially chloro and fluoro), hydroxy, alkoxy, keto, acyl, cyano, mercapto, alkylmercapto, dialkylamino, nitro, nitroso, and sulphoxy. The alkyl groups of these substituents may be further substituted.

Preferably $R^1$ is an optionally substituted alkyl or alkenyl group. Preferably $R^1$ is an optionally substituted alkyl group. Preferably $R^1$ is an optionally substituted alkyl or alkenyl group having from 1 to 7 carbon atoms, preferably from 1 to 6 carbon atoms, more preferably from 1 to 5 carbon atoms, suitably from 1 to 4 carbon atoms, preferably from 1 to 3 carbon atoms, more preferably from 1 to 2 carbon atoms.

Preferably $R^1$ is an optionally substituted alkyl or alkenyl group, preferably having from 1 to 6, preferably from 1 to 4 carbon atoms. Preferably $R^1$ is an alkyl group. It may be a substituted alkyl group, for example a hydroxy substituted alkyl group. Preferably $R^1$ is an unsubstituted alkyl group or a hydroxy alkyl group. More Preferably $R^1$ is an unsubstituted alkyl group. The alkyl chain may be straight-chained or branched. Preferably $R^1$ is selected from methyl, ethyl, propyl and butyl, including isomers thereof. Most preferably $R^1$ is methyl.

In some embodiments $R^1$, R and N together form an aromatic ring and the quaternary ammonium salt may have the structure:

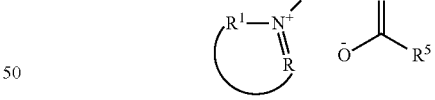

In such embodiments the total number of carbon atoms in groups R and $R^1$ is less than 19. An example of such a compound is a methyl pyridinium salt.

Preferably $R^2$ is an optionally substituted alkyl, alkenyl or aryl group, preferably having from 1 to 6, preferably from 1 to 4 carbon atoms. Preferably $R^2$ is an optionally substituted alkyl group. In some preferred embodiments $R^2$ is a hydroxy substituted alkyl group. Most preferably $R^2$ is a 2-hydroxyalkyl group. Suitably $R^2$ is selected from 2-hydroxyethyl, 2-hydroxypropyl 3-propoxy-2-hydroxy propyl and 2-hydroxybutyl. In one especially preferred embodiment $R^2$ is 2-hydroxybutyl. In one preferred embodiment $R^2$ is 3-propoxy-2-hydroxypropyl.

In some preferred embodiments $R^2$ is an unsubstituted alkyl group. The alkyl group may be straight chained or branched. Preferably $R^2$ is selected from methyl, ethyl, propyl and butyl, including isomers thereof. In one preferred embodiment $R^2$ is methyl.

The group R together with N forms a heterocycle having less than 12 carbon atoms.

R together with N may form an aliphatic heterocyclic group or an aromatic heterocyclic group. Thus they form a heterocyclic ring. There may be one or more further heteroatoms in the ring. Suitably the ring may include one or more further atoms selected from N, O and S.

The heterocyclic group formed by R and N may be substituted or unsubstituted; i.e. there may be one or more substituents bonded to atoms that form the ring. Suitable substituents include halo (especially chloro and fluro); hydroxy, alkoxy, keto, acyl, cyano, mercapto, alkylmercapto, alkyl, alkenyl, aryl, dialkylamino, alkylamino, nitro, nitroso, and sulphoxy. The alkyl, alkenyl and aryl groups of these substituents may be further substituted.

The heterocyclic group may be substituted with a further cyclic group i.e. it may be part of a bicyclic heterocyclic group.

In some preferred embodiments the heterocyclic group formed by N and R is not substituted.

Preferably the group formed by R and N is a heterocyclic group having from 3 to 12 atoms in the ring. The atoms in the ring include carbon atoms and other atoms. Preferably the heterocyclic ring includes 3 to 10 atoms, preferably 4 to 8, more preferably 5 to 7 atoms.

In some preferred embodiments the heterocyclic group contains only carbon and nitrogen atoms within the ring.

The heterocyclic group formed by R and N may be aliphatic or aromatic.

In some preferred embodiments R and N together form an aliphatic or aromatic heterocycle having 5 to 7 atoms in the ring.

Suitable aliphatic heterocyclic groups include those based on pyrrolidine, piperidine, morpholine and piperazine.

Suitable aliphatic heterocyclic groups include unsaturated heterocycles that are not aromatic. i.e. they may contain one or more double bonds, for example those based on dihydropyrrole.

Suitable aromatic heterocyclic groups including those based on pyrrole, pyridine, imidazole, pyrimidine, isoxazole, quinolone, oxazole, and pyrazole.

In especially preferred embodiments R and N together form an imidazole moiety or a pyrrolidine moiety.

Suitably R contains 3 to 11 carbon atoms (and optional heteroatoms with the ring), preferably 3 to 10 carbon atoms, preferably 3 to 9 carbon atoms, suitably 3 to 8 carbon atoms, preferably 3 to 7 carbon atoms, more preferably 3 to 6 carbon atoms, for example 3 to 5 or 3 to 4 carbon atoms.

Preferably R contains less than 8 carbon atoms.

The anion of the quaternary ammonium salts of the present invention is carboxylate group of formula $R^5COO—$. This is suitably the residue of an acid of formula $R^5COOH$. $R^5$ may comprise one or more additional acid or ester groups. It may be a monoacid, a diacid or a polyacid. It may be a monoester of a diacid or a partial ester of a polyacid. Thus $R^5$ may be —R'H, —R'COO$^-$, —R'COOH, —R'COOR", R'(COOR")$_n$ wherein each R' is independently an optionally substituted hydrocarbyl group, each R" may independently be H or an optionally substituted hydrocarbyl group and n is at least 1.

$R^5$ may be hydrogen or an optionally substituted hydrocarbyl group.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon groups, that is, substituents containing non-hydrocarbon groups which, in the context of this invention, do not alter the predominantly hydrocarbon nature of the substituent (e.g., halo (especially chloro and fluoro), hydroxy, alkoxy, keto, acyl, cyano, mercapto, alkylmercapto, amino, alkylamino, nitro, nitroso, and sulphoxy);

(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

$R^5$ is preferably selected from hydrogen and an optionally substituted alkyl, alkenyl or aryl group.

In some embodiments $R^5$ is an optionally substituted phenol residue. For example $R^5$ may be a 2-hydroxyphenyl group.

In one embodiment $R^5$ is COOR$^0$ where $R^0$ is a $C_1$ to $C_4$ alkyl group. In one embodiment $R^5$ is a 2-(methylcarboxy)-phenyl group.

Thus the anion $R^5COO—$ of the quaternary ammonium salt may be the residue of an ester of salicylic acid, oxalic acid or phthalic acid.

$R^5$ may be hydrogen and the anion is a formic acid residue. In some embodiments $R^5$ is a low molecular weight alkyl or alkenyl group having 1 to 8, preferably 1 to 6, preferably 1 to 4, for example 1 or 2 carbon atoms. The alkyl or alkenyl group may be straight chain or branched.

The present inventors were very surprised to find that embodiments of the present invention in which $R^5$ has less than 8 carbon atoms, for example less than 5 carbon atoms, gave excellent deposit control in modern diesel engines, since conventional wisdom would lead the skilled person to believe that a deposit control additive must include a long-chain hydrocarbyl group.

The anion $R^5COO—$ may be the residue of a monoacid, a diacid or a polyacid. It may be the residue of a monoester of a diacid or a partial ester of a polyacid.

In some embodiments $R^5$ is an optionally substituted $C_6$ to $C_{50}$ alkyl or alkenyl group, preferably a $C_6$ to $C_{40}$ alkyl or alkenyl group, more preferably a $C_8$ to $C_{36}$ alkyl or alkenyl group, preferably a $C_8$ to $C_{30}$ alkyl or alkenyl group, suitably a $C_{10}$ to $C_{24}$ alkyl or alkenyl group, for example a $C_{10}$ to $C_{20}$ alkyl or alkenyl group. The alkyl or alkenyl group may be straight chain or branched.

In some embodiments $R^5COO—$ may be the residue of a diacid or a monoester of a diacid, for example the residue of an optionally substituted phthalic acid or succinic acid derivative. Some preferred species are hydrocarbyl substituted phthalic acid or succinic acid derivatives wherein the hydrocarbyl substituent has a molecular weight of from 100 to 5000, preferably from 300 to 4000, suitably from 450 to 2500, for example from 500 to 2000 or from 600 to 1500.

In some embodiments $R^5COO—$ may be the residue of a polyacid or a partial ester of a polyacid, for example the residue of an optionally substituted pyromellitic acid derivative. Some preferred species are hydrocarbyl substituted pyromellitic acid derivatives wherein the hydrocarbyl substituent has a molecular weight of from 100 to 5000, preferably from 300 to 4000, suitably from 450 to 2500, for example from 500 to 2000 or from 600 to 1500.

In some embodiments $R^5$ is $CHR^{11}CHR^{12}COOR^{13}$ wherein each of $R^{11}$, $R^{12}$ and $R^{13}$ is hydrogen or an optionally substituted hydrocarbyl group. Preferably one of $R^{11}$ and $R^{12}$ is hydrogen and the other is an optionally substituted hydrocarbyl group. In one embodiment the optionally substituted hydrocarbyl group is preferably a polyisobutenyl group, preferably having a molecular weight of from 100 to 5000, preferably from 300 to 4000, suitably from 450 to 2500, for example from 500 to 2000 or from 600 to 1500.

In one embodiment the hydrocarbyl group ($R^{11}$ or $R^{12}$) is an alkyl or alkenyl group having 6 to 30 carbon atoms, preferably 10 to 26 carbon atoms, more preferably 12 to 24 carbon atoms, suitably 16 to 20 carbon atoms, for example 18 carbon atoms.

In one embodiment the hydrocarbyl group ($R^{11}$ or $R^{12}$) is an alkyl or alkenyl group having 6 to 50 carbon atoms, preferably 12 to 40 carbon atoms, more preferably 18 to 36 carbon atoms, suitably 24 to 36 carbon atoms, for example 30 carbon atoms.

The skilled person will appreciate that commercial sources of acids including hydrocarbyl chains often contain mixtures of homologues, in which minor amounts of alkyl chains having greater or fewer carbon atoms are also present.

In some embodiments $R^{13}$ is hydrogen. In some embodiments $R^{13}$ is an optionally substituted alkyl group, preferably having 1 to 20 carbon atoms. Suitably $R^{13}$ is an unsubstituted alkyl group, preferably having 1 to 12 carbon atoms. In one embodiment $R^{13}$ is a 2-ethyl hexyl group. In another embodiment $R^{13}$ is methyl.

In one especially preferred embodiment $R^5$ is methyl. In another especially preferred embodiment $R^5$ is a $C_{17}$ alkenyl group.

The quaternary ammonium compounds of the present invention may be prepared by any suitable method. Such methods are known to the person skilled in the art.

Suitably the quaternary ammonium salts of the present invention are prepared by the reaction of a tertiary amine of formula $R\!=\!\!=\!\!NR^1$ with a quaternising agent. For the avoidance of doubt the structure "$R\!=\!\!=\!\!NR^1$" is used to indicate that the group forms 2 bonds to N, not that it forms a double bond.

The quaternary ammonium salts of the present invention may be prepared by reaction of a tertiary amine with a quaternising agent selected from dialkyl sulfates, benzyl halides, hydrocarbyl substituted carbonates, alkyl halides, alkyl sulfonates, sultones, hydrocarbyl substituted phosphates, hydrocarbyl substituted borates, alkyl nitrites, alkyl nitrates, hydroxides, N-oxides or mixtures thereof, followed by an anion exchange reaction.

However in preferred embodiments the quaternary ammonium salt of the present invention is prepared by reacting a cyclic tertiary amine of formula $R\!=\!\!=\!\!NR^1$ with a quaternising agent selected from:
(i) an ester of formula $R^5COOR^2$;
(ii) a carbonate compound of formula $R^4OCOOR^2$ and then a carboxylic acid of formula $R^5COOH$; and
(iii) an epoxide having less than 8 carbon atoms and a carboxylic acid of formula $R^5COOH$;
wherein R, $R^1$, $R^2$, $R^5$ are as defined herein and $R^4$ is an optionally substituted hydrocarbyl group.

The present invention may thus provide a method of preparing a quaternary ammonium salt of the first aspect, the method comprising reacting a cyclic tertiary amine of formula $R\!=\!\!=\!\!NR^1$ with a quaternising agent selected from:
(i) an ester of formula $R^5COOR^2$;
(ii) a carbonate compound of formula $R^4OCOOR^2$ and then a carboxylic acid of formula $R^5COOH$; and
(iii) an epoxide having less than 8 carbon atoms and a carboxylic acid of formula $R^5COOH$;
wherein R, $R^1$, $R^2$, $R^5$ are as defined herein and $R^4$ is an optionally substituted hydrocarbyl group.

The compound of formula $R\!=\!\!=\!\!NR^1$ is a cyclic tertiary amine. By this we mean to refer to an amine group in which the nitrogen atom is part of a heterocyclic ring and is preferably further bonded to another group.

Suitably the compound of formula $R\!=\!\!=\!\!NR^1$ is a cyclic tertiary amine having less than 18 carbon atoms. Preferably it has less than 16 carbon atoms, suitably less than 14 carbon atoms, preferably less than 12 carbon atoms, for example less than 10 carbon atoms, less than 8 carbon atoms or less than 6 carbon atoms.

Suitably the compound of formula $R\!=\!\!=\!\!NR^1$ is an N-substituted heterocyclic amine. Preferably it is an N-alkyl heterocyclic amine having 5 to 7 atoms in the heterocyclic ring.

In some preferred embodiments the tertiary amine is an N-methyl cyclic amine including a heterocyclic ring moiety may include one or more further heteroatoms such as O, N or S and may be aliphatic or non-aromatic.

There are many different compounds of this type and these will be known to the person skilled in the art.

Some suitable amines of formula $R\!=\!\!=\!\!NR^1$ for use herein are based on N-alkyl heterocycles, for example N-methyl heterocycles, selected from pyrrolidine, piperidine, morpholine, piperazine, pyrrole, imidazole and dihydropyrrole. These compounds have the following structures:

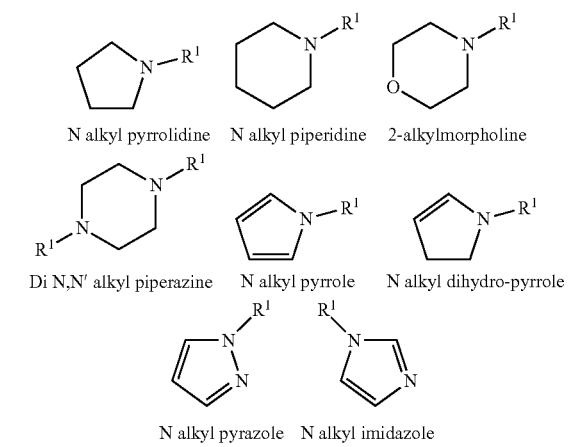

Other suitable amines include those based on the above in which the heterocyclic ring includes one or more further alkyl, alkenyl or aryl substituents, provided the total number of carbon atoms in the tertiary amine is less than 19. For example compounds which include one, two or three methyl groups bonded to carbon atoms within the heterocyclic ring are within the scope of the invention.

Some suitable amines of formula R═NR¹ for use herein are based on heterocycles in which R¹, R and N together form an aromatic ring, for example those based on piperidine, pyrimidine, isoxazole and oxazole.

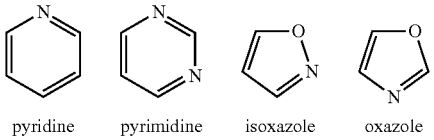

pyridine   pyrimidine   isoxazole   oxazole

Other suitable amines include those based on the above in which the heterocyclic ring includes one or more further alkyl, alkenyl or aryl substituents, provided the total number of carbon atoms in the tertiary amine is less than 19.

Examples of suitable amines of formula R═NR¹ for use in preparing the quaternary ammonium salts include a 1-methyl pyrrolidine, 1,2-dimethylpyrrolidine, 1,3-dimethylpyrrolidine, 1,2,3-trimethylpyrrolidine, 1,2,4-trimethylpyrrolidine, 1,2,5-trimethylpyrrolidine, 1,3,4-trimethylpyrrolidine, 1,2,3,4-tetramethylpyrrolidine, 1,2,3,5-tetramethylpyrrolidine, 2-ethyl-1-methylpyrrolidine, 3-ethyl-1-methylpyrrolidine, 2-ethyl-1,3-dimethylpyrrolidine, 2-ethyl-1,4-dimethylpyrrolidine, 2-ethyl-1,5-dimethylpyrrolidine, 3-ethyl-1,2-dimethylpyrrolidine, 3-ethyl-1,4-dimethylpyrrolidine, 4-ethyl-1,2-dimethylpyrrolidine, 1-methyl-2-propylpyrrolidine, 1-methyl-3-propylpyrrolidine, 2-isopropyl-1-methylpyrrolidine and 3-isopropyl-1-methylpyrrolidine, 1-methylpiperidine, 1,2-dimethylpiperidine, 1,3-dimethylpiperidine, 1,4-dimethylpiperidine, 1,2,3-trimethylpiperidine, 1,2,4-trimethylpiperidine, 1,2,5-trimethylpiperidine, 1,2,6-trimethylpiperidine, 2-ethyl-1-methylpiperidine, 3-ethyl-1-methylpiperidine, 4-ethyl-1-methylpiperidine, 4-methyl morpholine, 2,4-dimethylmorpholine, 3,4-dimethylmorpholine, 2,3,4-trimethylmorpholine, 2,4,5-trimethylmorpholine, 2,4,6-trimethylmorpholine, 3,4,5-trimethylmorpholine, 2-ethyl-4-methylmorpholine, 3-ethyl-4-methylmorpholine, 1,4-dimethylpiperazine, 1,2,4-trimethylpiperazine, 1,2,3,4-tetramethylpiperazine, 1,2,4,6-tetramethylpiperazine, 1-methyl-1H-pyrrole, 1,2-dimethyl-1H-pyrrole, 1,3-dimethyl-1H-pyrrole, 1,2,3-trimethyl-1H-pyrrole, 1,2,4-trimethyl-1H-pyrrole, 1,2,5-trimethyl-1H-pyrrole, 1,3,4-trimethyl-1H-pyrrole, 1,2,3,4-tetramethyl-1H-pyrrole, 1,2,3,5-tetramethyl-1H-pyrrole, 1-methyl-2,3-dihydro-1H-pyrrole, 1,5-dimethyl-2,3-dihydro-1H-pyrrole, 1,4-dimethyl-2,3-dihydro-1H-pyrrole, 1,3-dimethyl-2,3-dihydro-1H-pyrrole, 1,2-dimethyl-2,3-dihydro-1H-pyrrole, 1,4,5-trimethyl-2,3-dihydro-1H-pyrrole, 1,3,5-trimethyl-2,3-dihydro-1H-pyrrole, 1,2,5-trimethyl-2,3-dihydro-1H-pyrrole, 1,3,4-trimethyl-2,3-dihydro-1H-pyrrole, 1,2,4-trimethyl-2,3-dihydro-1H-pyrrole, 1,2,3-trimethyl-2,3-dihydro-1H-pyrrole, 1,3,4,5-tetramethyl-2,3-dihydro-1H-pyrrole, 1,2,4,5-tetramethyl-2,3-dihydro-1H-pyrrole, 1,2,3,5-tetramethyl-2,3-dihydro-1H-pyrrole, 1,2,3,4-tetramethyl-2,3-dihydro-1H-pyrrole, 5-ethyl-1-methyl-2,3-dihydro-1H-pyrrole, 4-ethyl-1-methyl-2,3-dihydro-1H-pyrrole, 3-ethyl-1-methyl-2,3-dihydro-1H-pyrrole, 2-ethyl-1-methyl-2,3-dihydro-1H-pyrrole, 5-ethyl-1,4-dimethyl-2,3-dihydro-1H-pyrrole, 5-ethyl-1,3-dimethyl-2,3-dihydro-1H-pyrrole, 5-ethyl-1,2-dimethyl-2,3-dihydro-1H-pyrrole, 4-ethyl-1,5-dimethyl-2,3-dihydro-1H-pyrrole, 4-ethyl-1,3-dimethyl-2,3-dihydro-1H-pyrrole, 4-ethyl-1,2-dimethyl-2,3-dihydro-1H-pyrrole, 3-ethyl-1,5-dimethyl-2,3-dihydro-1H-pyrrole, 3-ethyl-1,4-dimethyl-2,3-dihydro-1H-pyrrole, 3-ethyl-1,2-dimethyl-2, 3-dihydro-1H-pyrrole, 2-ethyl-1,5-dimethyl-2,3-dihydro-1H-pyrrole, 2-ethyl-1,4-dimethyl-2,3-dihydro-1H-pyrrole, 2-ethyl-1,3-dimethyl-2,3-dihydro-1H-pyrrole, 1-methyl-5-propyl-2,3-dihydro-1H-pyrrole, 1-methyl-4-propyl-2,3-dihydro-1H-pyrrole, 1-methyl-3-propyl-2,3-dihydro-1H-pyrrole, 1-methyl-2-propyl-2,3-dihydro-1H-pyrrole, 5-isopropyl-1-methyl-2,3-dihydro-1H-pyrrole, 4-isopropyl-1-methyl-2,3-dihydro-1H-pyrrole, 3-isopropyl-1-methyl-2,3-dihydro-1H-pyrrole, 2-isopropyl-1-methyl-2,3-dihydro-1H-pyrrole, pyridine, 1-methyl pyridine, 2-methyl pyridine, 3-methyl pyridine, 2,3-dimethyl pyridine, 2,4-dimethylpyridine, 2,5-dimethylpyridine, 2,6-dimethylpyridine, 3,4-dimethylpyridine, 3,5-dimethylpyridine, 2-ethyl pyridine, 3-ethyl pyridine and 4-ethyl pyridine, a pyrimidine, 2-methylpyrimidine, 4-methylpyrimidine, 5-methylpyrimidine, 2,4-dimethylpyrimidine, 2,5-dimethylpyrimidine, 4,5-dimethylpyrimidine, 4,6-dimethylpyrimidine, 2-ethylpyrimidine, 4-ethylpyrimidine, 5-ethylpyrimidine, isoxazole, 3-methylisoxazole, 4-methylisoxazole, 5-methylisoxazole, 3,4-dimethylisoxazole, 3,5-dimethylisoxazole, 4,5-dimethylisoxazole, 3,4,5-trimethylisoxazole, 3-ethylisoxazole, 4-ethylisoxazole, 5-ethyl isoxazole, 3-ethyl-4-methylisoxazole, 3-ethyl-5-methylisoxazole, 4-ethyl-3-methylisoxazole, 4-ethyl-5-methylisoxazole, 5-ethyl-3-methylisoxazole, 5-ethyl-4-methylisoxazole, 3-propylisoxazole, 4-propylisoxazole, 5-propylisoxazole, 3-isopropylisoxazole, 4-isopropyl isozazole, 5-isopropylisoxazole, 1-methyl imidazole, 1,2-dimethyl-1H-imidazole, 1,4-dimethyl-1H-imidazole, 1,5-dimethyl-1H-imidazole, 1,2,4-trimethyl-1H-imidazole, 1,2,5-trimethyl-1H-imidazole, 1,4,5-trimethyl-1H-imidazole, 2-ethyl-1-methyl-1H-imidazole, 4-ethyl-1-methyl-1H-imidazole, 5-ethyl-1-methyl-1H-imidazole, 1-ethyl-1H-imidazole, 1-ethyl-2-methyl-1H-imidazole, 1-ethyl-4-methyl-1H-imidazole, 1-ethyl-5-methyl-1H-imidazole, 1-methyl-1H-pyrazole, 1,3-dimethyl-1H-pyrazole, 1,4-dimethyl-1H-pyrazole, 1,5-dimethyl-1H-pyrazole, 1,3,4-trimethyl-1H-pyrazole, 1,3,5-trimethyl-1H-pyrazole, 1,4,5-trimethyl-1H-pyrazole.

Other suitable compounds for use herein are are similar to those listed above in which one or more of the methyl substituents is replaced with a different alkyl group, for example an ethyl or propyl substituent.

Tertiary amine compounds including primary or secondary amine groups are within the scope of the invention provided these groups do not prevent quaternisation of the tertiary amine species.

The tertiary amine compounds of formula R═NR¹ preferably do not include any free primary or secondary amine groups. The tertiary amine compound of formula R═NR¹ may contain more than one tertiary amine group.

Some preferred compounds of formula R═NR¹ include 1-methyl pyrrolidine, 1-methylimidazole, 1,2-dimethyl-1H-imidazole, pyridine and mixtures and isomers thereof. 8-hydroxyquinoline could also be used.

Especially preferred tertiary amine compounds of formula R═NR¹ include methyl pyrollidine and methyl imidazole.

Other suitable compounds would be known to the person skilled in the art.

In one embodiment the quaternising agent is (i) an ester of formula $R^5COOR^2$.

In such embodiments $R^2$ is a $C_1$ to $C_7$ alkyl group and $R^5$ is the residue of a carboxylic acid selected from a substituted aromatic carboxylic acid, an α-hydroxycarboxylic acid and a polycarboxylic acid.

Preferred ester quaternising agents are compounds of formula (X):

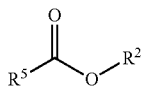

in which $R^5$ and $R^2$ are as previously defined herein. The compound of formula (X) is suitably an ester of a carboxylic acid capable of reacting with a tertiary amine to form a quaternary ammonium salt.

Suitable quaternising agents include esters of carboxylic acids having a pKa of 3.5 or less.

The compound of formula (X) is preferably an ester of a carboxylic acid selected from a substituted aromatic carboxylic acid, an α-hydroxycarboxylic acid and a polycarboxylic acid.

In some preferred embodiments the compound of formula (X) is an ester of a substituted aromatic carboxylic acid and thus $R^5$ is a substituted aryl group.

Especially preferred compounds of formula (X) are lower alkyl esters of salicylic acid such as methyl salicylate, ethyl salicylate, n and i-propyl salicylate, and butyl salicylate, preferably methyl salicylate.

In some embodiments the compound of formula (X) is an ester of an α-hydroxycarboxylic acid. In such embodiments the compound has the structure:

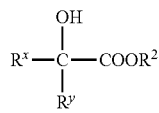

wherein $R^x$ and $R^y$ are the same or different and each is selected from hydrogen, alkyl, alkenyl, or aryl. Compounds of this type suitable for use herein are described in EP 1254889.

A preferred compound of this type is methyl 2-hydroxyisobutyrate.

In some embodiments the compound of formula (X) is an ester of a polycarboxylic acid. In this definition we mean to include dicarboxylic acids and carboxylic acids having more than 2 acidic moieties.

One especially preferred compound of formula (X) is dimethyl oxalate.

The ester quaternising agent may be selected from an ester of a carboxylic acid selected from one or more of oxalic acid, phthalic acid, tartaric acid, salicylic acid, maleic acid, malonic acid, citric acid, nitrobenzoic acid, aminobenzoic acid and 2,4,6-trihydroxybenzoic acid.

Preferred ester quaternising agents include dimethyl oxalate, methyl 2-nitrobenzoate, dimethylphthalate, dimethyltartrate and methyl salicylate.

In some embodiments the quaternary ammonium salts are prepared by reacting a tertiary amine of formula R=$NR^1$ with (ii) a carbonate of formula $R^4OCOOR^2$ and then with a carboxylic acid of formula $R^5COOH$. $R^2$ is as defined above. $R^4$ is preferably an optionally substituted alkyl alkenyl or aryl group having up to 30 carbon atoms. Preferably $R^4$ is an optionally substituted alkyl group. Preferably $R^4$ is an alkyl group having up to 24 carbon atoms, preferably up to 20 carbon atoms, suitably up to 16 carbon atoms, preferably up to 12 carbon atoms, suitably up to 8, for example up to 6 or up to 4 carbon atoms.

Preferably $R^4$ is an unsubstituted alkyl group. In one embodiment $R^4$ may be the same or different to $R^2$. Preferably $R^4$ is the same as $R^2$. Preferred carbonates are diethyl carbonate and dimethyl carbonate. Dimethyl carbonate is especially preferred. Once the tertiary amine has been reacted with a carbonate quaternising group the resulting salt is then reacted with a carboxylic acid of formula $R^5COOH$ to provide a compound of the first aspect.

The carboxylic acid of formula $R^5COOH$ may be a very small simple molecule. In some embodiments it may be a simple fatty acid compound. However it may also be a more complex molecule including additional acid functional groups.

Examples of suitable small simple acids include formic acid, acetic acid, propionic acid and butyric acid.

Examples of suitable fatty acids include caprylic acid, capris acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, arachidonic acid, eicosapentaenoic acid, erucic acid, undecylenic acid and docosahexenoic acid.

Suitable complex acids include optionally substituted phthalic acid and succinic acid derivatives.

In embodiments in which the acid includes more than one acid functional group the further groups may be present as the free acid or the ester. Where there is more than one free acid group there is suitably an equivalent number of cations.

In some preferred embodiments the quaternising agent is (iii) the combination of an epoxide and a carboxylic acid of formula $R^5COOH$.

Suitably the quaternary ammonium salts of the present invention are prepared by the reaction of a tertiary amine of formula R=$NR^1$ with an epoxide and $R^2$ is the residue of the epoxide.

The present invention suitably provides a quaternary ammonium compound which is the reaction product of:
(a) a cyclic tertiary amine having less than 19 carbon atoms;
(b) an epoxide having less than 8 carbon atoms; and
(c) a carboxylic acid of formula $R^5COOH$; wherein $R^5$ is hydrogen or an optionally substituted hydrocarbyl group.

According to a second aspect of the present invention there is provided a method of preparing a quaternary ammonium salt, the method comprising reacting (a) a cyclic tertiary amine having less than 19 carbon atoms with (b) an epoxide having less than 8 carbon atoms in the presence of (c) a carboxylic acid of formula $R^5COOH$; wherein $R^5$ is hydrogen or an optionally substituted hydrocarbyl group.

Preferred features of the second aspect of the invention are as defined in relation to the first aspect. Further preferred features of the invention will now be described which apply to the first and second aspects.

Component (a) is a cyclic tertiary amine having less than 19 carbon atoms.

Suitably the cyclic tertiary amine (a) has the formula R=$NR^1$ wherein $R^1$ is an optionally substituted alkyl, alkenyl or aryl group having less than 8 carbons and R together with N forms an aliphatic or aromatic heterocycle having less 12 carbon atoms. $R^1$ and the heterocycle formed by R and N are preferably as described in relation to the first aspect.

Especially preferred tertiary amine compounds for use as component (a) include methyl pyrollidine and methyl imidazole.

Any suitable epoxide compound having less than 8 carbon atoms may be used as component (b). Suitable epoxide compounds are those of formula:

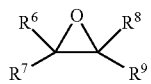

wherein each of $R^6$, $R^7$, $R^8$, $R^9$ is independently selected from hydrogen or an optionally substituted alkyl, alkenyl or aryl group.

At least one of $R^6$, $R^7$, $R^8$ and $R^9$ is hydrogen. Preferably at least two of $R^6$, $R^7$, $R^8$ and $R^9$ are hydrogen. Most preferably three of of $R^6$, $R^7$, $R^8$ and $R^9$ are hydrogen. of $R^6$, $R^7$, $R^8$ and $R^9$ may be all hydrogen.

In the structure above and the definitions which follow $R^6$ and $R^7$ are interchangeable and thus when these groups are different either enantiomer or diastereomer may be used as component (b).

In the structure above and the definitions which follow $R^8$ and $R^9$ are interchangeable and thus when these groups are different either enantiomer or diastereomer may be used as component (b).

Preferably $R^6$ is hydrogen or an optionally substituted alkyl, alkenyl or aryl group. Most preferably $R^6$ is hydrogen.

Preferably $R^7$ is hydrogen or an optionally substituted alkyl, alkenyl or aryl group. Most preferably $R^7$ is hydrogen.

Preferably $R^8$ is hydrogen or an optionally substituted alkyl, alkenyl or aryl group. Most preferably $R^8$ is hydrogen.

Preferably $R^9$ is hydrogen or an optionally substituted alkyl, alkenyl or aryl group. Preferably $R^9$ is an alkyl group having 1 to 5 carbon atoms. In some embodiments $R^9$ may include an oxygen atom in the carbon chain, i.e. $R^9$ may include an ether functional group.

Preferred epoxide compounds for use as component (b) include ethylene oxide, propylene oxide, butylene oxide, pentylene oxide, hexylene oxide and heptylene oxide. These may be provided as appropriate in any isomeric form or as a mixture of isomers. Also useful are glycidyl ether compounds, for example isopropyl glycidyl ether.

In some especially preferred embodiments component (b) is selected from 1,2-epoxy butane and isopropyl glycidyl ether.

Component (c) used to prepare the quaternary ammonium salts of the present invention is a carboxylic acid of formula $R^5COOH$.

Component (c) includes a carboxylic acid functional group. it may be a very small simple molecule. In some embodiments component (c) may be a simple fatty acid compound. However component (c) may also be a more complex molecule including additional acid functional groups.

For the avoidance of doubt component (c) is an acid which activates the alkylating agent (b) and forms the anionic counterion of the quaternary ammonium salt.

Example of suitable small simple acids for use as component (c) include formic acid, acetic acid, propionic acid and butyric acid.

Suitable fatty acids for use as component (c) include caprylic acid, capris acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, arachidonic acid, eicosapentaenoic acid, erucic acid, undecylenic acid and docosahexenoic acid.

Suitable complex acids for use as component (c) may be an optionally substituted phthalic acid and succinic acid derivatives.

In embodiments in which component (c) includes more than one acid functional group the further groups may be present as the free acid or the ester. Where there is more than one free acid group there is suitably an equivalent number of cations.

For example for in the case of diacid components (a), (b) and (c) are preferably reacted in a molar ratio of 2±0.5: 2±0.5:1; preferably 2±0.2:2±0.2:1, more preferably 2±0.1: 2±0.1:1.

The quaternary ammonium compounds of the present invention have been found to be effective as deposit control additives for use in fuel or lubricating additives.

Thus the present invention provides the use of a quaternary ammonium compound of the first aspect as an additive for fuel or lubricating oil compositions.

The present invention may provide the use of a quaternary ammonium compound of the first aspect as a deposit control additive for fuel or lubricating oil compositions.

The present invention may provide the use of a quaternary ammonium compound of the first aspect as a deposit control additive for lubricating oil compositions.

The present invention may provide the use of a quaternary ammonium compound of the first aspect as a deposit control additive for fuel compositions.

The present invention may provide the use of a quaternary ammonium compound of the first aspect as a deposit control additive for gasoline or diesel fuel compositions.

The present invention may provide the use of a quaternary ammonium compound of the first aspect as a deposit control additive for gasoline fuel compositions.

The present invention may provide the use of a quaternary ammonium compound of the first aspect as a deposit control additive for diesel fuel compositions.

According to a third aspect of the present invention there is provided an additive composition comprising a quaternary ammonium salt of the first aspect and a diluent or carrier.

The additive composition of the third aspect may be an additive composition for lubricating oil.

The additive composition of the third aspect may be an additive composition for gasoline.

Preferably the additive composition of the third aspect is an additive composition for diesel fuel.

The quaternary ammonium compound is suitably present in the additive composition in an amount of from 1 to 99 wt %, for example from 1 to 75 wt %.

The additive composition may comprise a mixture of two or more quaternary ammonium compounds of the present invention. In such embodiments the above amounts suitably refer to the total amount of all such compounds present in the composition.

The additive composition may include one or more further additives. These may be selected from antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers and conductivity improvers.

In some preferred embodiments the additive composition includes one or more further nitrogen-containing detergents.

The present invention may provide a fuel or lubricating oil composition comprising a quaternary ammonium salt of the first aspect.

According to a fourth aspect of the present invention there is provided a lubricating composition comprising an oil of lubricating viscosity and as an additive a quaternary ammonium salt of the first aspect.

Preferred features of the quaternary ammonium compound are as defined in relation to the first and second aspects.

The additive composition of the third aspect suitably upon dilution provides a lubricating composition of the fourth aspect.

According to a fifth aspect of the present invention there is provided a fuel composition comprising as an additive a quaternary ammonium salt of the first aspect.

Preferred features of the quaternary ammonium compound are as defined in relation to the first and second aspects.

The additive composition of the third aspect suitably upon dilution provides a fuel composition of the fifth aspect.

The present invention may further provide a method of preparing a fuel composition, the method comprising preparing a quaternary ammonium salt according to the method of the second aspect, and mixing the quaternary ammonium salt into the fuel.

Additives of the invention may be added to diesel fuel at any convenient place in the supply chain. For examples, the additives may be added to fuel at the refinery, at a distribution terminal or after the fuel has left the distribution terminal. If the additive is added to the fuel after it has left the distribution terminal, this is termed an aftermarket application. Aftermarket applications include such circumstances as adding the additive to the fuel in the delivery tanker, directly to a customer's bulk storage tank, or directly to the end user's vehicle tank. Aftermarket applications may include supplying the fuel additive in small bottles suitable for direct addition to fuel storage tanks or vehicle tanks.

The composition of the present invention may be a gasoline composition or a diesel fuel composition. Preferably it is a diesel fuel composition.

By diesel fuel we include any fuel suitable for use in a diesel engine either for road use or non-road use. This includes but is not limited to fuels described as diesel, marine diesel, heavy fuel oil, industrial fuel oil, etc.

The diesel fuel composition of the present invention may comprise a petroleum-based fuel oil, especially a middle distillate fuel oil. Such distillate fuel oils generally boil within the range of from 110° C. to 500° C., e.g. 150° C. to 400° C. The diesel fuel may comprise atmospheric distillate or vacuum distillate, cracked gas oil, or a blend in any proportion of straight run and refinery streams such as thermally and/or catalytically cracked and hydro-cracked distillates.

The diesel fuel composition of the present invention may comprise non-renewable Fischer-Tropsch fuels such as those described as GTL (gas-to-liquid) fuels, CTL (coal-to-liquid) fuels and OTL (oil sands-to-liquid).

The diesel fuel composition of the present invention may comprise a renewable fuel such as a biofuel composition or biodiesel composition.

The diesel fuel composition may comprise 1st generation biodiesel. First generation biodiesel contains esters of, for example, vegetable oils, animal fats and used cooking fats. This form of biodiesel may be obtained by transesterification of oils, for example rapeseed oil, soybean oil, safflower oil, palm oil, corn oil, peanut oil, cotton seed oil, tallow, coconut oil, physic nut oil (Jatropha), sunflower seed oil, used cooking oils, hydrogenated vegetable oils or any mixture thereof, with an alcohol, usually a monoalcohol, usually in the presence of a catalyst.

The diesel fuel composition may comprise second generation biodiesel. Second generation biodiesel is derived from renewable resources such as vegetable oils and animal fats and processed, often in the refinery, often using hydroprocessing such as the H-Bio process developed by Petrobras. Second generation biodiesel may be similar in properties and quality to petroleum based fuel oil streams, for example renewable diesel produced from vegetable oils, animal fats etc. and marketed by ConocoPhillips as Renewable Diesel and by Neste as NExBTL.

The diesel fuel composition of the present invention may comprise third generation biodiesel. Third generation biodiesel utilises gasification and Fischer-Tropsch technology including those described as BTL (biomass-to-liquid) fuels. Third generation biodiesel does not differ widely from some second generation biodiesel, but aims to exploit the whole plant (biomass) and thereby widens the feedstock base.

The diesel fuel composition may contain blends of any or all of the above diesel fuel compositions.

In some embodiments the diesel fuel composition of the present invention may be a blended diesel fuel comprising bio-diesel. In such blends the bio-diesel may be present in an amount of, for example up to 0.5%, up to 1%, up to 2%, up to 3%, up to 4%, up to 5%, up to 10%, up to 20%, up to 30%, up to 40%, up to 50%, up to 60%, up to 70%, up to 80%, up to 90%, up to 95% or up to 99%.

In some embodiments the fuel composition may comprise neat biodiesel.

In some embodiments the fuel composition may comprise a neat GTL fuel.

In some embodiments the diesel fuel composition may comprise a secondary fuel, for example ethanol. Preferably however the diesel fuel composition does not contain ethanol.

The diesel fuel composition of the present invention may contain a relatively high sulphur content, for example greater than 0.05% by weight, such as 0.1% or 0.2%.

However in preferred embodiments the diesel fuel has a sulphur content of at most 0.05% by weight, more preferably of at most 0.035% by weight, especially of at most 0.015%. Fuels with even lower levels of sulphur are also suitable such as, fuels with less than 50 ppm sulphur by weight, preferably less than 20 ppm, for example 10 ppm or less.

Suitably the quaternary ammonium salt additive is present in the diesel fuel composition in an amount of at least 0.1 ppm, preferably at least 1 ppm, more preferably at least 5 ppm, suitably at least 10 ppm, for example at least 20 ppm or at least 25 ppm.

Suitably the quaternary ammonium salt additive is present in the diesel fuel composition in an amount of less than 10000 ppm, preferably less than 1000 ppm, preferably less than 500 ppm, preferably less than 250 ppm, suitably less than 200 ppm, for example less than 150 ppm or less than 100 ppm.

The diesel fuel composition of the fifth aspect of the present invention may comprise a mixture of two or more quaternary ammonium salts of the first aspect. In such embodiments the above amounts refer to the total amounts of all such additives present in the composition.

The diesel fuel composition of the present invention may include one or more further additives such as those which are commonly found in diesel fuels. These include, for example, antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers and conductivity improvers. Examples of suitable amounts of each of these types of additives will be known to the person skilled in the art.

In some preferred embodiments the diesel fuel composition of the present invention comprises one or more further detergents. Nitrogen-containing detergents are preferred.

The one or more further detergents may be selected from:
(i) an additional quaternary ammonium salt additive which is not a quaternary ammonium compound of the first aspect;
(ii) the product of a Mannich reaction between an aldehyde, an amine and an optionally substituted phenol;
(iii) the reaction product of a carboxylic acid-derived acylating agent and an amine;
(iv) the reaction product of a carboxylic acid-derived acylating agent and hydrazine;
(v) a salt formed by the reaction of a carboxylic acid with di-n-butylamine or tri-n-butylamine;
(vi) the reaction product of a hydrocarbyl-substituted dicarboxylic acid or anhydride and an amine compound or salt which product comprises at least one amino triazole group; and
(vii) a substituted polyaromatic detergent additive.

In some embodiments the diesel fuel composition comprises an additional quaternary ammonium salt additive which is not a quaternary ammonium compound of the first aspect.

The additional quaternary ammonium salt additive is suitably the reaction product of a nitrogen-containing species having at least one tertiary amine group and a quaternising agent.

The nitrogen containing species may be selected from:
(x) the reaction product of a hydrocarbyl-substituted acylating agent and a compound comprising at least one tertiary amine group and a primary amine, secondary amine or alcohol group;
(y) a Mannich reaction product comprising a tertiary amine group; and
(z) a polyalkylene substituted amine having at least one tertiary amine group.

Examples of quaternary ammonium salt and methods for preparing the same are described in the following patents, which are hereby incorporated by reference, US2008/0307698, US2008/0052985, US2008/0113890 and US2013/031827.

Component (x) may be regarded as the reaction product of a hydrocarbyl-substituted acylating agent and a compound having an oxygen or nitrogen atom capable of condensing with said acylating agent and further having a tertiary amino group. Preferred features of these compounds are as described above in relation to tertiary amine component (a) used to prepare the quaternary ammonium salt additives of the present invention.

The preparation of some suitable quaternary ammonium salt additives in which the nitrogen-containing species includes component (x) is described in WO 2006/135881 and WO2011/095819.

Component (y) is a Mannich reaction product having a tertiary amine. The preparation of quaternary ammonium salts formed from nitrogen-containing species including component (y) is described in US 2008/0052985. Preferred features of these compounds are as described above in relation to tertiary amine component (a) used to prepare the quaternary ammonium salt additives of the present invention.

The preparation of quaternary ammonium salt additives in which the nitrogen-containing species includes component (z) is described for example in US 2008/0113890. Preferred features of these compounds are as described above in relation to tertiary amine component (a) used to prepare the quaternary ammonium salt additives of the present invention.

To form the additional quaternary ammonium salt additives (I), the nitrogen containing species having a tertiary amine group is reacted with a quaternizing agent.

The quaternising agent may suitably be selected from esters and non-esters.

In some preferred embodiments, quaternising agents used to form the quaternary ammonium salt additives of the present invention are esters.

Preferred ester quaternising agents are compounds of formula (III):

(III)

in which R is an optionally substituted alkyl, alkenyl, aryl or alkylaryl group and $R^1$ is a $C_1$ to $C_{22}$ alkyl, aryl or alkylaryl group. The compound of formula (III) is suitably an ester of a carboxylic acid capable of reacting with a tertiary amine to form a quaternary ammonium salt.

Suitable quaternising agents include esters of carboxylic acids having a pKa of 3.5 or less.

The compound of formula (III) is preferably an ester of a carboxylic acid selected from a substituted aromatic carboxylic acid, an α-hydroxycarboxylic acid and a polycarboxylic acid.

In some preferred embodiments the compound of formula (III) is an ester of a substituted aromatic carboxylic acid and thus R is a substituted aryl group.

Especially preferred compounds of formula (III) are lower alkyl esters of salicylic acid such as methyl salicylate, ethyl salicylate, n and i-propyl salicylate, and butyl salicylate, preferably methyl salicylate.

In some embodiments the compound of formula (III) is an ester of an α-hydroxycarboxylic acid. In such embodiments the compound has the structure:

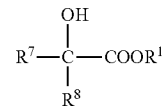

wherein $R^7$ and $R^8$ are the same or different and each is selected from hydrogen, alkyl, alkenyl, aralkyl or aryl. Compounds of this type suitable for use herein are described in EP 1254889.

A preferred compound of this type is methyl 2-hydroxyisobutyrate.

In some embodiments the compound of formula (III) is an ester of a polycarboxylic acid. In this definition we mean to include dicarboxylic acids and carboxylic acids having more than 2 acidic moieties.

One especially preferred compound of formula (III) is dimethyl oxalate.

The ester quaternising agent may be selected from an ester of a carboxylic acid selected from one or more of oxalic acid, phthalic acid, tartaric acid, salicylic acid, maleic acid, malonic acid, citric acid, nitrobenzoic acid, aminobenzoic acid and 2, 4, 6-trihydroxybenzoic acid.

Preferred ester quaternising agents include dimethyl oxalate, methyl 2-nitrobenzoate, dimethyl phthalate, dimethyl tartrate and methyl salicylate.

Suitable non-ester quaternising agents include dialkyl sulfates, benzyl halides, hydrocarbyl substituted carbonates, hydrocarbyl substituted epoxides in combination with an acid, alkyl halides, alkyl sulfonates, sultones, hydrocarbyl substituted phosphates, hydrocarbyl substituted borates, alkyl nitrites, alkyl nitrates, hydroxides, N-oxides or mixtures thereof.

In some embodiments the quaternary ammonium salt may be prepared from, for example, an alkyl or benzyl halide (especially a chloride) and then subjected to an ion exchange reaction to provide a different anion as part of the quaternary ammonium salt. Such a method may be suitable to prepare quaternary ammonium hydroxides, alkoxides, nitrites or nitrates.

Preferred non-ester quaternising agents include dialkyl sulfates, benzyl halides, hydrocarbyl substituted carbonates, hydrocarbyl substituted epoxides in combination with an acid, alkyl halides, alkyl sulfonates, sultones, hydrocarbyl substituted phosphates, hydrocarbyl substituted borates, N-oxides or mixtures thereof.

Suitable dialkyl sulfates for use herein as quaternising agents include those including alkyl groups having 1 to 10 carbons atoms in the alkyl chain. A preferred compound is dimethyl sulfate.

Suitable benzyl halides include chlorides, bromides and iodides. A preferred compound is benzyl bromide.

Suitable hydrocarbyl substituted carbonates may include two hydrocarbyl groups, which may be the same or different. Preferred compounds of this type include diethyl carbonate and dimethyl carbonate.

Suitable hydrocarbyl substituted epoxides have the formula:

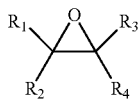

wherein each of $R^1$, $R^2$, $R^3$ and $R^4$ is independently hydrogen or a hydrocarbyl group having 1 to 50 carbon atoms. Examples of suitable epoxides include ethylene oxide, propylene oxide, butylene oxide, styrene oxide and stilbene oxide. The hydrocarbyl epoxides are used as quaternising agents in combination with an acid. In such embodiments the acid is not an acid of the type defined in relation to component (c) used to prepare the quaternary ammonium salts of the present invention.

In embodiments in which the hydrocarbyl substituted acylating agent has more than one acyl group no separate acid needs to be added. However in other embodiments an acid such as acetic acid may be used.

Especially preferred epoxide quaternising agents are propylene oxide and styrene oxide.

Suitable sultones include propane sultone and butane sultone.

Suitable hydrocarbyl substituted phosphates include dialkyl phosphates, trialkyl phosphates and O,O-dialkyl dithiophosphates.

Suitable hydrocarbyl substituted borate groups include alkyl borates having 1 to 12 carbon atoms.

Preferred alkyl nitrites and alkyl nitrates have 1 to 12 carbon atoms.

Preferably the non-ester quaternising agent is selected from dialkyl sulfates, benzyl halides, hydrocarbyl substituted carbonates, hydrocarbyl substituted epoxides in combination with an acid, and mixtures thereof.

Especially preferred non-ester quaternising agents for use herein are hydrocarbyl substituted epoxides in combination with an acid. These may include embodiments in which a separate acid is provided or embodiments in which the acid is provided by the tertiary amine compound that is being quaternised. Preferably the acid is provided by the tertiary amine molecule that is being quaternised.

Preferred quaternising agents for use herein include dimethyl oxalate, methyl 2-nitrobenzoate, methyl salicylate and styrene oxide or propylene oxide optionally in combination with an additional acid.

An especially preferred additional quaternary ammonium salt for use herein is formed by reacting methyl salicylate or dimethyl oxalate with the reaction product of a polyisobutylene-substituted succinic anhydride having a PIB molecular weight of 700 to 1300 and dimethylaminopropylamine.

Other suitable additional quaternary ammonium salts include quaternised terpolymers, for example as described in US2011/0258917; quaternised copolymers, for example as described in US2011/0315107; and the acid-free quaternised nitrogen compounds disclosed in US2012/0010112.

Further suitable additional quaternary ammonium compounds for use in the present invention include the quaternary ammonium compounds described in the applicants copending application WO2013/017889.

In some embodiments the diesel fuel composition comprises the product of a Mannich reaction between an aldehyde, an amine and an optionally substituted phenol. This Mannich reaction product is suitably not a quaternary ammonium salt.

Preferably the aldehyde component used to prepare the Mannich additive is an aliphatic aldehyde. Preferably the aldehyde has 1 to 10 carbon atoms. Most preferably the aldehyde is formaldehyde.

The amine used to prepare the Mannich additive is preferably a polyamine. This may be selected from any compound including two or more amine groups. Preferably the polyamine is a polyalkylene polyamine, preferably a polyethylene polyamine. Most preferably the polyamine comprises tetraethylenepentamine or ethylenediamine.

The optionally substituted phenol component used to prepare the Mannich additive may be substituted with 0 to 4 groups on the aromatic ring (in addition to the phenol OH). For example it may be a hydrocarbyl-substituted cresol. Most preferably the phenol component is a mono-substituted phenol. Preferably it is a hydrocarbyl substituted phenol. Preferred hydrocarbyl substituents are alkyl substituents having 4 to 28 carbon atoms, especially 10 to 14 carbon atoms. Other preferred hydrocarbyl substituents are polyalkenyl substituents such polyisobutenyl substituents having an average molecular weight of from 400 to 2500, for example from 500 to 1500.

In some embodiments the diesel fuel composition comprises the reaction product of a carboxylic acid-derived acylating agent and an amine.

These may also be referred to herein in general as acylated nitrogen-containing compounds.

Suitable acylated nitrogen-containing compounds may be made by reacting a carboxylic acid acylating agent with an amine and are known to those skilled in the art.

Preferred acylated nitrogen-containing compounds are hydrocarbyl substituted. The hydrocarbyl substituent may be in either the carboxylic acid acylating agent derived portion of the molecule or in the amine derived portion of the molecule, or both. Preferably, however, it is in the acylating agent portion. A preferred class of acylated nitrogen-containing compounds suitable for use in the present invention are those formed by the reaction of an acylating agent having a hydrocarbyl substituent of at least 8 carbon atoms and a compound comprising at least one primary or secondary amine group.

The acylating agent may be a mono- or polycarboxylic acid (or reactive equivalent thereof) for example a substituted succinic, phthalic or propionic acid or anhydride.

The term "hydrocarbyl" is previously defined herein. The hydrocarbyl substituent in such acylating agents preferably comprises at least 10, more preferably at least 12, for example at least 30 or at least 40 carbon atoms. It may comprise up to about 200 carbon atoms. Preferably the hydrocarbyl substituent of the acylating agent has a number average molecular weight (Mn) of between 170 to 2800, for example from 250 to 1500, preferably from 500 to 1500 and more preferably 500 to 1100. An Mn of 700 to 1300 is especially preferred. In a particularly preferred embodiment, the hydrocarbyl substituent has a number average molecular weight of 700-1000, preferably 700-850 for example 750.

Preferred hydrocarbyl-based substituents are polyisobutenes. Such compounds are known to the person skilled in the art.

Preferred hydrocarbyl substituted acylating agents are polyisobutenyl succinic anhydrides. These compounds are commonly referred to as "PIBSAs" and are known to the person skilled in the art.

Conventional polyisobutenes and so-called "highly-reactive" polyisobutenes are suitable for use in the invention.

Especially preferred PIBSAs are those having a PIB molecular weight (Mn) of from 300 to 2800, preferably from 450 to 2300, more preferably from 500 to 1300.

To prepare these additives the carboxylic acid-derived acylating agent is reacted with an amine. Suitably it is reacted with a primary or secondary amine. Examples of suitable amines are known to the person skilled in the art and include polyalkylene polyamines, heterocyclic-substituted polyamines and aromatic polyamines.

Preferred amines are polyethylene polyamines including ethylenediamine, diethylenetriamine, triethylenetetramine, tetraethylenepentamine, pentaethylenehexamine, hexaethylene-heptamine, and mixtures and isomers thereof.

In preferred embodiments the reaction product of the carboxylic acid derived acylating agent and an amine includes at least one primary or secondary amine group.

A preferred acylated nitrogen-containing compound for use herein is prepared by reacting a poly(isobutene)-substituted succinic acid-derived acylating agent (e.g., anhydride, acid, ester, etc.) wherein the poly(isobutene) substituent has a number average molecular weight (Mn) of between 170 to 2800 with a mixture of ethylene polyamines having 2 to about 9 amino nitrogen atoms, preferably about 2 to about 8 nitrogen atoms, per ethylene polyamine and about 1 to about 8 ethylene groups. These acylated nitrogen compounds are suitably formed by the reaction of a molar ratio of acylating agent:amino compound of from 10:1 to 1:10, preferably from 5:1 to 1:5, more preferably from 2:1 to 1:2 and most preferably from 2:1 to 1:1. In especially preferred embodiments, the acylated nitrogen compounds are formed by the reaction of acylating agent to amino compound in a molar ratio of from 1.8:1 to 1:1.2, preferably from 1.6:1 to 1:1.2, more preferably from 1.4:1 to 1:1.1 and most preferably from 1.2:1 to 1:1. Acylated amino compounds of this type and their preparation are well known to those skilled in the art and are described in for example EP0565285 and U.S. Pat. No. 5,925,151.

In some preferred embodiments the composition comprises a detergent of the type formed by the reaction of a polyisobutene-substituted succinic acid-derived acylating agent and a polyethylene polyamine. Suitable compounds are, for example, described in WO2009/040583.

In some embodiments the diesel fuel composition comprises the reaction product of a carboxylic acid-derived acylating agent and hydrazine.

Suitably the additive comprises the reaction product between a hydrocarbyl-substituted succinic acid or anhydride and hydrazine.

Preferably, the hydrocarbyl group of the hydrocarbyl-substituted succinic acid or anhydride comprises a $C_8$-$C_{36}$ group, preferably a $C_8$-$C_{18}$ group. Alternatively, the hydrocarbyl group may be a polyisobutylene group with a number average molecular weight of between 200 and 2500, preferably between 800 and 1200.

Hydrazine has the formula $NH_2$—$NH_2$. Hydrazine may be hydrated or non-hydrated. Hydrazine monohydrate is preferred.

The reaction between the hydrocarbyl-substituted succinic acid or anhydride and hydrazine produces a variety of products, such as is disclosed in US 2008/0060259.

In some embodiments the diesel fuel composition comprises a salt formed by the reaction of a carboxylic acid with di-n-butylamine or tri-n-butylamine. Exemplary compounds of this type are described in US 2008/0060608.

Such additives may suitably be the di-n-butylamine or tri-n-butylamine salt of a fatty acid of the formula $[R'(COOH)_x]_y$, where each R' is a independently a hydrocarbon group of between 2 and 45 carbon atoms, and x is an integer between 1 and 4.

In a preferred embodiment, the carboxylic acid comprises tall oil fatty acid (TOFA).

Further preferred features of additives of this type are described in EP1900795.

In some embodiments the diesel fuel composition comprises the reaction product of a hydrocarbyl-substituted dicarboxylic acid or anhydride and an amine compound or salt which product comprises at least one amino triazole group.

Additives of this type are suitably the reaction product of a hydrocarbyl substituted dicarboxylic acid or anhydride and an amine compound having the formula:

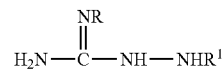

wherein R is selected from the group consisting of a hydrogen and a hydrocarbyl group containing from about 1 to about 15 carbon atoms, and $R^1$ is selected from the group consisting of hydrogen and a hydrocarbyl group containing from about 1 to about 20 carbon atoms.

The additive suitably comprises the reaction product of an amine compound having the formula:

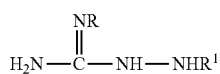

and a hydrocarbyl carbonyl compound of the formula:

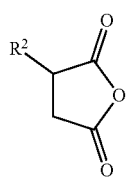

wherein $R^2$ is a hydrocarbyl group having a number average molecular weight ranging from about 100 to about 5000, preferably from 200 to 3000.

Without being bound by theory, it is believed that the reaction product of the amine and hydrocarbyl carbonyl compound is an aminotriazole, such as a bis-aminotriazole compound of the formula:

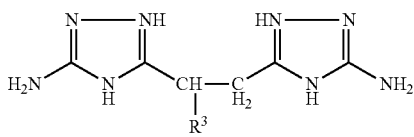

including tautomers having a number average molecular weight ranging from about 200 to about 3000 containing from about 40 to about 80 carbon atoms. The five-membered ring of the triazole is considered to be aromatic.

Further preferred features of additive compounds of this type are as defined in US2009/0282731.

In some embodiments the diesel fuel composition comprises a substituted polyaromatic detergent additive.

One preferred compound of this type is the reaction product of an ethoxylated naphthol and paraformaldehyde which is then reacted with a hydrocarbyl substituted acylating agent.

Further preferred features of these detergents are described in EP1884556.

In some embodiments the fuel composition may be a gasoline fuel composition.

Suitably the quaternary ammonium salt additive is present in the gasoline fuel composition in an amount of at least 0.1 ppm, preferably at least 1 ppm, more preferably at least 5 ppm, suitably at least 10 ppm, for example at least 20 ppm or at least 25 ppm.

Suitably the quaternary ammonium salt additive is present in the gasoline fuel composition in an amount of less than 10000 ppm, preferably less than 1000 ppm, preferably less than 500 ppm, preferably less than 250 ppm, suitably less than 200 ppm, for example less than 150 ppm, or less than 100 ppm.

The gasoline fuel composition of the fifth aspect of the present invention may comprise a mixture of two or more quaternary ammonium salts of the first aspect. In such embodiments the above amounts refer to the total amounts of all such additives present in the composition.

In such embodiments the composition may comprise one or more gasoline detergents selected from:
(p) hydrocarbyl-substituted polyoxyalkylene amines or polyetheramines;
(q) acylated nitrogen compounds which are the reaction product of a carboxylic acid-derived acylating agent and an amine;
(r) hydrocarbyl-substituted amines wherein the hydrocarbyl substituent is substantially aliphatic and contains at least 8 carbon atoms;
(s) Mannich base additives comprising nitrogen-containing condensates of a phenol, aldehyde and primary or secondary amine;
(t) aromatic esters of a polyalkylphenoxyalkanol;
(u) an additional quaternary ammonium salt additive which is not a quaternary ammonium compound of the first aspect; and
(v) tertiary hydrocarbyl amines having a maximum of 30 carbon atoms.

Suitable hydrocarbyl-substituted polyoxyalkylene amines or polyetheramines (p) are described in U.S. Pat. Nos. 6,217,624 and 4,288,612. Other suitable polyetheramines are those taught in U.S. Pat. Nos. 5,089,029 and 5,112,364.

The gasoline composition of the present invention may comprise as an additive acylated nitrogen compounds (q) which are the reaction product of a carboxylic acid-derived acylating agent and an amine. Such compounds are preferably as previously defined herein in relation to component (iii) of the additives which may be added to the diesel fuel compositions of the invention.

Hydrocarbyl-substituted amines (r) suitable for use in the gasoline fuel compositions of the present invention are well known to those skilled in the art and are described in a number of patents. Among these are U.S. Pat. Nos. 3,275,554; 3,438,757; 3,454,555; 3,565,804; 3,755,433 and 3,822,209. These patents describe suitable hydrocarbyl amines for use in the present invention including their method of preparation.

The Mannich additives (s) comprise nitrogen-containing condensates of a phenol, aldehyde and primary or secondary amine, and are suitably as defined in relation to component (ii) of the additives suitable for use in diesel fuel compositions.

The gasoline compositions of the present invention may further comprise as additives (t) aromatic esters of a polyalkylphenoxyalkanol.

The aromatic ester component which may be employed additive composition is an aromatic ester of a polyalkylphenoxyalkanol and has the following general formula:

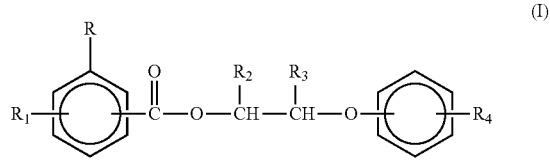

or a fuel-soluble salt(s) thereof wherein R is hydroxy, nitro or $-(CH_2)x-NR_5R_6$, wherein $R_5$ and $R_6$ are independently hydrogen or lower alkyl having 1 to 6 carbon atoms and x is 0 or 1;

$R_1$ is hydrogen, hydroxy, nitro or $-NR_7R_8$ wherein $R_7$ and $R_8$ are independently hydrogen or lower alkyl having 1 to 6 carbon atoms;

$R_2$ and $R_3$ are independently hydrogen or lower alkyl having 1 to 6 carbon atoms; and $R_4$ is a polyalkyl group having an average molecular weight in the range of about 450 to 5,000.

Preferred features of these aromatic ester compounds are as described in WO2011141731.

The additional quaternary ammonium salt additives (u) are suitably as defined in relation to component (i) of the additives suitable for use in diesel fuel compositions.

Tertiary hydrocarbyl amines (v) suitable for use in the gasoline fuel compositions of the present invention are tertiary amines of the formula $R^1R^2R^3N$ wherein $R^1$, $R^2$ and $R^3$ are the same or different $C_1$-$C_{20}$ hydrocarbyl residues and the total number of carbon atoms is no more than 30. Suitable examples are N,N dimethyl n dodecylamine, 3-(N, N-dimethylamino) propanol and N, N-di(2-hydroxyethyl)-oleylamine. Preferred features of these tertiary hydrocarbyl amines are as described in US2014/0123547.

The gasoline composition may further comprise a carrier oil.

The carrier oil may have any suitable molecular weight. A preferred molecular weight is in the range 500 to 5000.

In one embodiment the carrier oil may comprise an oil of lubricating viscosity, including natural or synthetic oils of lubricating viscosity, oil derived from hydrocracking, hydrogenation, hydrofinishing, unrefined, refined and re-refined oils, or mixtures thereof.

Natural oils include animal oils, vegetable oils, mineral oils or mixtures thereof. Synthetic oils may include hydrocarbon oils such as those produced by Fischer-Tropsch reactions and typically may be hydroisomerised Fischer-Tropsch hydrocarbons or waxes.

In another embodiment the carrier oil may comprise a polyether carrier oil. In a preferred embodiment the polyether carrier oil is a mono end-capped polyalkylene glycol, especially a mono end-capped polypropylene glycol. Carrier oils of this type will be known to the person skilled in the art.

The gasoline fuel compositions of the invention may contain one or more further additives conventionally added to gasoline, for example other detergents, dispersants, antioxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, conductivity improvers and combustion improvers.

The quaternary ammonium salts of the present invention are useful as deposit control additives for fuel and lubricating oil compositions. The inclusion of these additives in fuel compositions has been found to reduce deposits within engines in which the fuel is combusted. This may be achieved by preventing or reducing the formation of deposits, i.e. keeping the engine clean, or may be by the removal of existing deposits, i.e. cleaning up a fouled engine.

The quaternary ammonium compounds of the present invention have been found to be particularly effective in diesel engines, especially in modern diesel engines having a high pressure fuel system.

Due to consumer demand and legislation, diesel engines have in recent years become much more energy efficient, show improved performance and have reduced emissions.

These improvements in performance and emissions have been brought about by improvements in the combustion process. To achieve the fuel atomisation necessary for this improved combustion, fuel injection equipment has been developed which uses higher injection pressures and reduced fuel injector nozzle hole diameters. The fuel pressure at the injection nozzle is now commonly in excess of 1500 bar ($1.5 \times 10^8$ Pa). To achieve these pressures the work that must be done on the fuel also increases the temperature of the fuel. These high pressures and temperatures can cause degradation of the fuel. Furthermore, the timing, quantity and control of fuel injection has become increasingly precise. This precise fuel metering must be maintained to achieve optimal performance.

Diesel engines having high pressure fuel systems can include but are not limited to heavy duty diesel engines and smaller passenger car type diesel engines. Heavy duty diesel engines can include very powerful engines such as the MTU series 4000 diesel having 20 cylinder variants designed primarily for ships and power generation with power output up to 4300 kW or engines such as the Renault dXi 7 having 6 cylinders and a power output around 240 kW. A typical passenger car diesel engine is the Peugeot DW10 having 4 cylinders and power output of 100 kW or less depending on the variant.

In preferred diesel engines relating to this invention, a common feature is a high pressure fuel system. Typically pressures in excess of 1350 bar ($1.35 \times 10^8$ Pa) are used but often pressures of up to 2000 bar ($2 \times 10^8$ Pa) or more may exist.

Two non-limiting examples of such high pressure fuel systems are: the common rail injection system, in which the fuel is compressed utilizing a high-pressure pump that supplies it to the fuel injection valves through a common rail; and the unit injection system which integrates the high-pressure pump and fuel injection valve in one assembly, achieving the highest possible injection pressures exceeding 2000 bar ($2 \times 10^8$ Pa). In both systems, in pressurising the fuel, the fuel gets hot, often to temperatures around 100° C., or above.

In common rail systems, the fuel is stored at high pressure in the central accumulator rail or separate accumulators prior to being delivered to the injectors. Often, some of the heated fuel is returned to the low pressure side of the fuel system or returned to the fuel tank. In unit injection systems the fuel is compressed within the injector in order to generate the high injection pressures. This in turn increases the temperature of the fuel.

In both systems, fuel is present in the injector body prior to injection where it is heated further due to heat from the combustion chamber. The temperature of the fuel at the tip of the injector can be as high as 250-350° C.

Thus the fuel is stressed at pressures from 1350 bar ($1.35 \times 10^8$ Pa) to over 2000 bar ($2 \times 10^8$ Pa) and temperatures from around 100° C. to 350° C. prior to injection, sometimes being recirculated back within the fuel system thus increasing the time for which the fuel experiences these conditions.

A common problem with diesel engines is fouling of the injector, particularly the injector body, and the injector nozzle. Fouling may also occur in the fuel filter. Injector nozzle fouling occurs when the nozzle becomes blocked with deposits from the diesel fuel. Fouling of fuel filters may be related to the recirculation of fuel back to the fuel tank. Deposits increase with degradation of the fuel. Deposits may take the form of carbonaceous coke-like residues, lacquers or sticky or gum-like residues. Diesel fuels become more and more unstable the more they are heated, particularly if heated under pressure. Thus diesel engines having high pressure fuel systems may cause increased fuel degradation. In recent years the need to reduce emissions has led to the continual redesign of injection systems to help meet lower targets. This has led to increasingly complex injectors and lower tolerance to deposits.

The problem of injector fouling may occur when using any type of diesel fuels. However, some fuels may be particularly prone to cause fouling or fouling may occur more quickly when these fuels are used. For example, fuels containing biodiesel and those containing metallic species may lead to increased deposits.

When injectors become blocked or partially blocked, the delivery of fuel is less efficient and there is poor mixing of the fuel with the air. Over time this leads to a loss in power of the engine, increased exhaust emissions and poor fuel economy.

Deposits are known to occur in the spray channels of the injector, leading to reduced flow and power loss. As the size of the injector nozzle hole is reduced, the relative impact of deposit build up becomes more significant. Deposits are also known to occur at the injector tip. Here, they affect the fuel spray pattern and cause less effective combustion and associated higher emissions and increased fuel consumption.

In addition to these "external" injector deposits in the nozzle hole and at the injector tip which lead to reduced flow and power loss, deposits may occur within the injector body causing further problems. These deposits may be referred to as internal diesel injector deposits (or IDIDs). IDIDs occur inside the injector on the critical moving parts. They can hinder the movement of these parts affecting the timing and quantity of fuel injection. Since modern diesel engines operate under very precise conditions these deposits can have a significant impact on performance.

IDIDs cause a number of problems, including power loss and reduced fuel economy due to less than optimal fuel metering and combustion. Initially the user may experience cold start problems and/or rough engine running. These deposits can lead to more serious injector sticking. This occurs when the deposits stop parts of the injector from moving and thus the injector stops working. When several or all of the injectors stick the engine may fail completely.

It is known to add nitrogen-containing detergents to diesel fuel to reduce coking. Typical nitrogen-containing detergents include those formed by the reaction of a polyisobutylene-substituted succinic acid derivative with a polyalkylene polyamine. However, newer engines including finer injector nozzles are more sensitive and current diesel fuels may not be suitable for use with the new engines incorporating these smaller nozzle holes.

As mentioned above, the problem of injector fouling may be more likely to occur when using fuel compositions comprising metal species. Various metal species may be present in fuel compositions. This may be due to contamination of the fuel during manufacture, storage, transport or use or due to contamination of fuel additives. Metal species may also be added to fuels deliberately. For example transition metals are sometimes added as fuel borne catalysts, for example to improve the performance of diesel particulate filters.

The present inventors believe that problems of injector sticking occur when metal or ammonium species, particularly sodium species, react with carboxylic acid species in the fuel.

Sodium contamination of diesel fuel and the resultant formation of carboxylate salts is believed to be a major cause of injector sticking.

In preferred embodiments the diesel fuel compositions used in the present invention comprise sodium and/or calcium. Preferably they comprise sodium. The sodium and/or calcium is typically present in a total amount of from 0.01 to 50 ppm, preferably from 0.05 to 5 ppm preferably 0.1 to 2 ppm such as 0.1 to 1 ppm.

Other metal-containing species may also be present as a contaminant, for example through the corrosion of metal and metal oxide surfaces by acidic species present in the fuel or from lubricating oil. In use, fuels such as diesel fuels routinely come into contact with metal surfaces for example, in vehicle fuelling systems, fuel tanks, fuel transportation means etc. Typically, metal-containing contamination may comprise transition metals such as zinc, iron and copper; group I or group II metals and other metals such as lead.

The presence of metal containing species may give rise to fuel filter deposits and/or external injector deposits including injector tip deposits and/or nozzle deposits.

In addition to metal-containing contamination which may be present in diesel fuels there are circumstances where metal-containing species may deliberately be added to the fuel. For example, as is known in the art, metal-containing fuel-borne catalyst species may be added to aid with the regeneration of particulate traps. The presence of such catalysts may also give rise to injector deposits when the fuels are used in diesel engines having high pressure fuel systems.

Metal-containing contamination, depending on its source, may be in the form of insoluble particulates or soluble compounds or complexes. Metal-containing fuel-borne catalysts are often soluble compounds or complexes or colloidal species.

In some embodiments, the diesel fuel may comprise metal-containing species comprising a fuel-borne catalyst. Preferably, the fuel borne catalyst comprises one or more metals selected from iron, cerium, platinum, manganese, Group I and Group II metals e.g., calcium and strontium. Most preferably the fuel borne catalyst comprises a metal selected from iron and cerium.

In some embodiments, the diesel fuel may comprise metal-containing species comprising zinc. Zinc may be present in an amount of from 0.01 to 50 ppm, preferably from 0.05 to 5 ppm, more preferably 0.1 to 1.5 ppm.

Typically, the total amount of all metal-containing species in the diesel fuel, expressed in terms of the total weight of metal in the species, is between 0.1 and 50 ppm by weight, for example between 0.1 and 20 ppm, preferably between 0.1 and 10 ppm by weight, based on the weight of the diesel fuel.

It is advantageous to provide a diesel fuel composition which prevents or reduces the occurrence of deposits in a diesel engine. Such deposits may include "external" injector deposits such as deposits in and around the nozzle hole and at the injector tip and "internal" injector deposits or IDIDs. Such fuel compositions may be considered to perform a "keep clean" function i.e. they prevent or inhibit fouling. It is also be desirable to provide a diesel fuel composition which would help clean up deposits of these types. Such a fuel composition which when combusted in a diesel engine removes deposits therefrom thus effecting the "clean-up" of an already fouled engine.

As with "keep clean" properties, "clean-up" of a fouled engine may provide significant advantages. For example, superior clean up may lead to an increase in power and/or an increase in fuel economy. In addition removal of deposits from an engine, in particular from injectors may lead to an increase in interval time before injector maintenance or replacement is necessary thus reducing maintenance costs.

Although for the reasons mentioned above deposits on injectors is a particular problem found in modern diesel engines with high pressure fuels systems, it is desirable to provide a diesel fuel composition which also provides effective detergency in older traditional diesel engines such that a single fuel supplied at the pumps can be used in engines of all types.

It is also desirable that fuel compositions reduce the fouling of vehicle fuel filters. It is useful to provide compositions that prevent or inhibit the occurrence of fuel filter deposits i.e, provide a "keep clean" function. It is useful to provide compositions that remove existing deposits from fuel filter deposits i.e. provide a "clean up" function. Compositions able to provide both of these functions are especially useful.

According to a sixth aspect of the present invention there is provided a method of improving the performance of an engine, the method comprising combusting in said engine a fuel composition comprising as an additive a quaternary ammonium salt of formula:

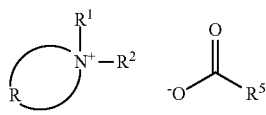

wherein each of $R^1$ and $R^2$ is independently selected from an optionally substituted alkyl, alkenyl or aryl group having less than 8 carbon atoms, R together with N forms an aliphatic or aromatic group having less than 12 carbon atoms and $R^5$ is hydrogen or an optionally substituted hydrocarbyl group.

Preferred features of the sixth aspect of the present invention are as defined in relation to the first, second, third and fifth aspects.

In the method of the fifth aspect the engine may be a gasoline engine and the fuel composition may be a gasoline fuel.

Preferably in the method of the fourth aspect the engine is a diesel engine and the fuel composition is a diesel fuel composition.

The method of the fourth aspect of the present invention is particularly effective at improving the performance of a modern diesel engine having a high pressure fuel system.

Such diesel engines may be characterised in a number of ways.

Such engines are typically equipped with fuel injection equipment meeting or exceeding "Euro 5" emissions legislation or equivalent legislation in US or other countries.

Such engines are typically equipped with fuel injectors having a plurality of apertures, each aperture having an inlet and an outlet.

Such engines may be characterised by apertures which are tapered such that the inlet diameter of the spray-holes is greater than the outlet diameter.

Such modern engines may be characterised by apertures having an outlet diameter of less than 500 μm, preferably less than 200 μm, more preferably less than 150 μm, preferably less than 100 μm, most preferably less than 80 μm or less.

Such modern diesel engines may be characterised by apertures where an inner edge of the inlet is rounded.

Such modern diesel engines may be characterised by the injector having more than one aperture, suitably more than 2 apertures, preferably more than 4 apertures, for example 6 or more apertures.

Such modern diesel engines may be characterised by an operating tip temperature in excess of 250° C.

Such modern diesel engines may be characterised by a a fuel injection system which provides a fuel pressure of more than 1350 bar, preferably more than 1500 bar, more preferably more than 2000 bar. Preferably, the diesel engine has fuel injection system which comprises a common rail injection system.

The method of the present invention preferably improves the performance of an engine having one or more of the above-described characteristics.

The method of the present invention improves the performance of an engine. This improvement in performance is suitably achieved by reducing deposits in the engine.

The present invention may therefore provide a method of combating deposits in an engine comprising combusting in said engine a fuel composition of the fourth aspect.

The sixth aspect of the present invention preferably relates to a method of combating deposits in an engine, preferably a diesel engine. Combating deposits may involve reducing or the preventing of the formation of deposits in an engine compared to when running the engine using unadditised fuel. Such a method may be regarded as achieving "keep clean" performance.

Combating deposits may involve the removal of existing deposits in an engine. This may be regarded as achieving "clean up" performance.

In especially preferred embodiments the method of the sixth aspect of the present invention may be used to provide "keep clean" and "clean up" performance.

As explained above deposits may occur at different places within a modern diesel engine, for example a modern diesel engine.

The present invention is particularly useful in the prevention or reduction or removal of internal deposits in injectors of engines operating at high pressures and temperatures in which fuel may be recirculated and which comprise a plurality of fine apertures through which the fuel is delivered to the engine. The present invention finds utility in engines for heavy duty vehicles and passenger vehicles. Passenger vehicles incorporating a high speed direct injection (or HSDI) engine may for example benefit from the present invention.

The present invention may also provide improved performance in modern diesel engines having a high pressure fuel system by controlling external injector deposits, for example those occurring in the injector nozzle and/or at the injector tip. The ability to provide control of internal injector deposits and external injector deposits is a useful advantage of the present invention.

Suitably the present invention may reduce or prevent the formation of external injector deposits. It may therefore provide "keep clean" performance in relation to external injector deposits.

Suitably the present invention may reduce or remove existing external injector deposits. It may therefore provide "clean up" performance in relation to external injector deposits.

Suitably the present invention may reduce or prevent the formation of internal diesel injector deposits. It may therefore provide "keep clean" performance in relation to internal diesel injector deposits.

Suitably the present invention may reduce or remove existing internal diesel injector deposits. It may therefore provide "clean up" performance in relation to internal diesel injector deposits.

The present invention may also combat deposits on vehicle fuel filters. This may include reducing or preventing the formation of deposits ("keep clean" performance) or the reduction or removal of existing deposits ("clean up" performance).

The diesel fuel compositions of the present invention may also provide improved performance when used with traditional diesel engines. Preferably the improved performance is achieved when using the diesel fuel compositions in modern diesel engines having high pressure fuel systems and when using the compositions in traditional diesel engines. This is important because it allows a single fuel to be provided that can be used in new engines and older vehicles.

The removal or reduction of IDIDs according to the present invention will lead to an improvement in performance of the engine.

The improvement in performance of the diesel engine system may be measured by a number of ways. Suitable methods will depend on the type of engine and whether "keep clean" and/or "clean up" performance is measured.

An improvement in "keep clean" performance may be measured by comparison with a base fuel. "Clean up" performance can be observed by an improvement in performance of an already fouled engine.

The effectiveness of fuel additives is often assessed using a controlled engine test.

In Europe the Co-ordinating European Council for the development of performance tests for transportation fuels, lubricants and other fluids (the industry body known as CEC), has developed a test for additives for modern diesel engines such as HSDI engines. The CEC F-98-08 test is used to assess whether diesel fuel is suitable for use in engines meeting new European Union emissions regulations known as the "Euro 5" regulations. The test is based on a Peugeot DW10 engine using Euro 5 injectors, and is commonly referred to as DW10 test. This test measures power loss in the engine due to deposits on the injectors, and is further described in example 6.

Preferably the use of the fuel composition of the present invention leads to reduced deposits in the DW10 test. For "keep clean" performance a reduction in the occurrence of deposits is preferably observed.

For "clean up" performance removal of deposits is preferably observed. The DW10 test is used to measure the power loss in modern diesel engines having a high pressure fuel system.

Suitably the use of a fuel composition of the present invention may provide a "keep clean" performance in modern diesel engines, that is the formation of deposits on the injectors of these engines may be inhibited or prevented. Preferably this performance is such that a power loss of less than 5%, preferably less than 2% is observed after 32 hours as measured by the DW10 test.

In some embodiments, the present invention may provide a power gain. Suitably when combusting a fuel composition according to the present invention a power gain in the DW10 test is observed compared to when combusting an unadditised base fuel and with clean injectors. Suitably a power gain of at least 0.5%, preferably at least 1% is achieved within 4 hours, preferably within 2 hours. Details of the methods used to measure the power gain are given in example 8.

Suitably the use of a fuel composition of the present invention may provide a "clean up" performance in modern diesel engines that is deposits on the injectors of an already fouled engine may be removed. Preferably this performance is such that the power of a fouled engine may be returned to within 1% of the level achieved when using clean injectors within 16 hours, preferably 12 hours, more preferably 8 hours as measured in the DW10 test.

Preferably rapid "clean-up" may be achieved in which the power is returned to within 1% of the level observed using clean injectors within 4 hours, preferably within 2 hours.

In some preferred embodiments, clean up may also provide a power increase. Thus a fouled engine may be treated to remove the existing deposits and provide an additional power gain.

Clean injectors can include new injectors or injectors which have been removed and physically cleaned, for example in an ultrasound bath.

According to a seventh aspect of the present invention there the use of an additive in a fuel composition to improve the performance of an engine combusting said fuel composition wherein the additive is a quaternary ammonium salt of formula:

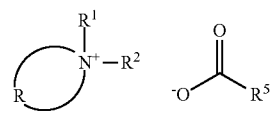

wherein each of $R^1$ and $R^2$ is independently selected from an optionally substituted alkyl, alkenyl or aryl group having less than 8 carbon atoms, R together with N forms an aliphatic or aromatic group having less than 12 carbon atoms and $R^5$ is hydrogen or an optionally substituted hydrocarbyl group.

Preferred features of the seventh aspect of the present invention are as defined in relation to the first, second, third and fifth aspects, and especially as defined in relation to the sixth aspect.

The invention will now be further described with reference to the following non-limiting examples. In the examples which follow the values given in parts per million (ppm) for treat rates denote active agent amount, not the amount of a formulation as added, and containing an active agent. All parts per million are by weight.

EXAMPLE 1

Additive A19, Bis (1,1-dimethylpyrrolidin-1-ium) octadecenyl succinate was prepared as follows:

A sample of octadenyl succinic acid was prepared by hydrolysis of a xylene solution of a commercial sample of the corresponding anhydride before removing volatiles by rotary evaporation leaving a cream-coloured solid. The acid value was determined, by wet analysis, to be 5.27 mMol/g (calc. 5.32).

N-methyl pyrrolidine (2.865 g, 33.7 mMol), dimethyl carbonate (12.298 g, 136.6 mMol) and methanol (10 cm3) were charged to a tube and heated, with stirring, for one hour at 130° C., under autogeneous pressure. The formation of a methyl carbonate salt was confirmed by FTIR (characteristic absorbance at 1651 $cm^{-1}$).

The solution of 1,1-dimethylpyrrolidin-1-ium methyl carbonate was transferred to a round-bottom flask. Octadecenyl succinic acid (6.282 g, 33.1 mMol of acidity) was added. On stirring and warming (oil bath, 45° C.) the solids dissolved, with gas evolution. After 60 minutes gas evolution had ceased. The solution was taken to dryness on a rotary evaporator (2 mBar, 90° C.), forming orange-brown waxy solids which were dissolved, with warming, in an equal mass of 2-ethyl hexanol. Mass balances and FTIR spectra were in accord with substantially complete formation of a carboxylate salt (absorbances at about 1575 and 1378 $cm^{-1}$)

EXAMPLE 2

Additive A21, Bis (N,N'-dimethyl imidazolium) octadecenyl succinate was prepared as follows:

N-methyl imidazole (2.544 g, 31 mMol), dimethyl carbonate (10.96 g, 122 mMol) and methanol (12.5 cm$^3$) were charged to a tube and heated, with stirring, under autogeneous pressure, at 160° C. for three hours. The formation of a methyl carbonate salt was confirmed by FTIR (absorbance at 1645 cm$^{-1}$).

Material from the tube was transferred to a round-bottom flask and reacted with a single equivalent (acid value basis, 0.5 molar equivalents) of octadecenyl succinic acid, as set out above. The material was stripped to dryness in the rotary evaporator (6 mBar, 90° C.). Mass balance was consistent with formation of the desired product in good yield. The material was dissolved, with strong heating, in an equal mass of 2-ethyl hexanol. The FTIR spectrum was consistent with formulation as the proposed carboxylate salt, with characteristic absorbances at 1569 and 1379 cm$^{-1}$.

EXAMPLE 3

Additives A16, A17 and A18 were each prepared as a 50% w/w solution in 2-ethyl hexanol as follows:

The succinic acid suspended in 2-ethylhexan-1-ol was placed in a boiling tube. One or two equivalents of cyclic tertiary amine and one or two equivalents of epoxide were added and the reaction heated at 95° C. for 6 hours. The product was confirmed via FTIR spectra.

The further compounds using the following acids, amines and epoxides:

| Additive | Acid | Amine added (molar equiv) | Epoxide added (molar equiv) |
|---|---|---|---|
| A16 | Octadecenylsuccinic acid | Methyl Pyrollidine (2) | 1,2-epoxybutane (2) |
| A17 | Octadecenylsuccinic acid | Methyl Pyrollidine (2) | Iso propyl glycidyl ether (2) |
| A18 | Octadecenylsuccinic acid | Methyl Imidazole (2) | Iso propyl glycidyl ether (2) |
| A22 | C30+ alpha olefin succinic acid | Methyl Pyrollidine (1) | 1,2-epoxybutane (1) |

The C30+ alpha olefin succinic acid is the reaction product of a terminal alkene consisting mainly of molecules having at least 30 carbon atoms and maleic anhydride. The alkene is available commercially from Chevron Phillips Chemical Company under the trade mark AlphaPlus® C30+.

EXAMPLE 4

Diesel fuel compositions were prepared comprising the additives listed in Table 1, added to aliquots all drawn from a common batch of RF06 base fuel.

TABLE 1

| Fuel Composition | Additive | (ppm active) |
|---|---|---|
| Comparative | C | 105 |
| 1 | A16 | 105 |
| 2 | A17 | 105 |
| 3 | A18 | 105 |
| 4 | A19 | 105 |
| 5 | A21 | 105 |
| 6 | A22 | 105 |

Additive C is a comparative low molecular weight succinimide detergent additive, that was prepared as follows:

Polyisobutylene succinic anhydride with a Mn of 360 ((442 g) was charged to a reactor followed by solvent Shellsol150 (442 g). 1 equivalent of tetraethylene pentamine (243 g) was added and the mixture stirred at 175 C for 3 hours whilst distilling off the water in a dean and stark condenser. The product was then discharged from the reactor.

Table 2 below shows the specification for RFO6 base fuel.

TABLE 2

| | | Limits | | |
|---|---|---|---|---|
| Property | Units | Min | Max | Method |
| Cetane Number | | 52.0 | 54.0 | EN ISO 5165 |
| Density at 15° C. | kg/m$^3$ | 833 | 837 | EN ISO 3675 |
| Distillation | | | | |
| 50% v/v Point | ° C. | 245 | — | |
| 95% v/v Point | ° C. | 345 | 350 | |
| FBP | ° C. | — | 370 | |
| Flash Point | ° C. | 55 | — | EN 22719 |
| Cold Filter Plugging Point | ° C. | — | −5 | EN 116 |
| Viscosity at 40° C. | mm$^2$/sec | 2.3 | 3.3 | EN ISO 3104 |
| Polycyclic Aromatic Hydrocarbons | % m/m | 3.0 | 6.0 | IP 391 |
| Sulphur Content | mg/kg | — | 10 | ASTM D 5453 |
| Copper Corrosion | | — | 1 | EN ISO 2160 |
| Conradson Carbon Residue on 10% Dist. Residue | % m/m | — | 0.2 | EN ISO 10370 |
| Ash Content | % m/m | — | 0.01 | EN ISO 6245 |
| Water Content | % m/m | — | 0.02 | EN ISO 12937 |
| Neutralisation (Strong Acid) Number | mg KOH/g | — | 0.02 | ASTM D 974 |
| Oxidation Stability | mg/mL | — | 0.025 | EN ISO 12205 |
| HFRR (WSD1,4) | µm | — | 400 | CEC F-06-A-96 |
| Fatty Acid Methyl Ester | | | prohibited | |

EXAMPLE 5

Each of the fuel compositions prepared in example 4 was tested using Jet Fuel Thermal Oxidation Test (JFTOT) equipment. In this test 800 ml of fuel is flowed over an aluminium tube heated to 260° C. at a pressure of approximately 540 psi (3.72×10$^6$ Pa). The test duration is 2.5 hours. At the end of test the aluminium tube is removed and the thickness of deposit compared to the comparative fuel.

The results are shown in table 2.

| Fuel Composition | Deposit Thickness (nm) |
|---|---|
| Comparative | 377 |
| 1 | 60 |
| 2 | 43 |
| 3 | 105 |
| 4 | 49 |
| 5 | 43 |
| 6 | 21 |

EXAMPLE 6

The performance of fuel compositions of the present invention in modern diesel engines having a high pressure fuel system may be tested according to the CECF-98-08 DW 10 method.

The engine of the injector fouling test is the PSA DW10BTED4. In summary, the engine characteristics are:

Design: Four cylinders in line, overhead camshaft, turbocharged with EGR

Capacity: 1998 cm$^3$

Combustion chamber: Four valves, bowl in piston, wall guided direct injection

Power: 100 kW at 4000 rpm

Torque: 320 Nm at 2000 rpm

Injection system: Common rail with piezo electronically controlled 6-hole injectors.

Max. pressure: 1600 bar (1.6×10$^8$ Pa). Proprietary design by SIEMENS VDO Emissions control: Conforms with Euro IV limit values when combined with exhaust gas post-treatment system (DPF)

This engine was chosen as a design representative of the modern European high-speed direct injection diesel engine capable of conforming to present and future European emissions requirements. The common rail injection system uses a highly efficient nozzle design with rounded inlet edges and conical spray holes for optimal hydraulic flow. This type of nozzle, when combined with high fuel pressure has allowed advances to be achieved in combustion efficiency, reduced noise and reduced fuel consumption, but are sensitive to influences that can disturb the fuel flow, such as deposit formation in the spray holes. The presence of these deposits causes a significant loss of engine power and increased raw emissions.

The test is run with a future injector design representative of anticipated Euro V injector technology.

It is considered necessary to establish a reliable baseline of injector condition before beginning fouling tests, so a sixteen hour running-in schedule for the test injectors is specified, using non-fouling reference fuel.

Full details of the CEC F-98-08 test method can be obtained from the CEC. The coking cycle is summarised below.

1. A warm up cycle (12 minutes) according to the following regime:

| Step | Duration (minutes) | Engine Speed (rpm) | Torque (Nm) |
| --- | --- | --- | --- |
| 1 | 2 | idle | <5 |
| 2 | 3 | 2000 | 50 |
| 3 | 4 | 3500 | 75 |
| 4 | 3 | 4000 | 100 |

2. 8 hrs of engine operation consisting of 8 repeats of the following cycle

| Step | Duration (minutes) | Engine Speed (rpm) | Load (%) | Torque (Nm) | Boost Air After IC (° C.) |
| --- | --- | --- | --- | --- | --- |
| 1 | 2 | 1750 | (20) | 62 | 45 |
| 2 | 7 | 3000 | (60) | 173 | 50 |
| 3 | 2 | 1750 | (20) | 62 | 45 |
| 4 | 7 | 3500 | (80) | 212 | 50 |
| 5 | 2 | 1750 | (20) | 62 | 45 |
| 6 | 10 | 4000 | 100 | * | 50 |
| 7 | 2 | 1250 | (10) | 20 | 43 |
| 8 | 7 | 3000 | 100 | * | 50 |
| 9 | 2 | 1250 | (10) | 20 | 43 |
| 10 | 10 | 2000 | 100 | * | 50 |
| 11 | 2 | 1250 | (10) | 20 | 43 |
| 12 | 7 | 4000 | 100 | * | 50 |

* for expected range see CEC method CEC-F-98-08

3. Cool down to idle in 60 seconds and idle for 10 seconds
4. 4 hrs soak period

The standard CEC F-98-08 test method consists of 32 hours engine operation corresponding to 4 repeats of steps 1-3 above, and 3 repeats of step 4. ie 56 hours total test time excluding warm ups and cool downs.

EXAMPLE 7

The effectiveness of the fuel compositions of the present invention in older engine types may be assessed using a standard industry test—CEC test method No. CEC F-23-A-01.

This test measures injector nozzle coking using a Peugeot XUD9 A/L Engine and provides a means of discriminating between fuels of different injector nozzle coking propensity. Nozzle coking is the result of carbon deposits forming between the injector needle and the needle seat. Deposition of the carbon deposit is due to exposure of the injector needle and seat to combustion gases, potentially causing undesirable variations in engine performance.

The Peugeot XUD9 A/L engine is a 4 cylinder indirect injection Diesel engine of 1.9 litre swept volume, obtained from Peugeot Citroen Motors specifically for the CEC PF023 method.

The test engine is fitted with cleaned injectors utilising unflatted injector needles. The airflow at various needle lift positions have been measured on a flow rig prior to test. The engine is operated for a period of 10 hours under cyclic conditions.

| Stage | Time (secs) | Speed (rpm) | Torque (Nm) |
| --- | --- | --- | --- |
| 1 | 30 | 1200 ± 30 | 10 ± 2 |
| 2 | 60 | 3000 ± 30 | 50 ± 2 |
| 3 | 60 | 1300 ± 30 | 35 ± 2 |
| 4 | 120 | 1850 ± 30 | 50 ± 2 |

The propensity of the fuel to promote deposit formation on the fuel injectors is determined by measuring the injector nozzle airflow again at the end of test, and comparing these values to those before test. The results are expressed in terms of percentage airflow reduction at various needle lift positions for all nozzles. The average value of the airflow reduction at 0.1 mm needle lift of all four nozzles is deemed the level of injector coking for a given fuel.

EXAMPLE 8

In Europe the Co-ordinating European Council for the development of performance tests for transportation fuels, lubricants and other fluids (the industry body known as CEC), has developed a new test for additives for modern diesel engines such as HSDI engines. The CEC F-110-xx[1] test is used to assess whether diesel fuel is suitable for use in engines meeting new European Union emissions regulations known as the "Euro 5" regulations. The test is based on a Peugeot DW10 engine using Euro 5 injectors, and is commonly referred to as DW10C test. This test measures the effects of deposits on the injectors specific to IDID's with respect to injector sticking.

[1] Test procedure still in draft format and final CEC issue number not yet available.

In this test thermocouples are positioned in the engine to enable the exhaust temperature of each cylinder to be measured. This, in conjunction with other measured parameters, allows injector sticking to be tested.

The engine of the injector fouling test is the PSA DW10CTED4/E5. In summary, the engine characteristics are:

Design: Four cylinders in line, overhead camshaft, turbocharged with EGR

Capacity: 1997 cm$^3$

Combustion chamber: Four valves, bowl in piston, wall guided direct injection

Power: 120 kW at 3750 rpm

Torque: 340 Nm at 2000 rpm

Injection system: Common rail with piezo electronically controlled 6-hole injectors.

Max. pressure: 1600 bar ($1.6 \times 10^8$ Pa). Proprietary design by Delphi

Emissions control: Conforms with Euro V limit values when combined with exhaust gas post-treatment system (DPF)

This engine was chosen as a design representative of the modern European high-speed direct injection diesel engine capable of conforming to present and future European emissions requirements. The common rail injection system uses a highly efficient nozzle design with rounded inlet edges and conical spray holes for optimal hydraulic flow. This type of nozzle, when combined with high fuel pressure has allowed advances to be achieved in combustion efficiency, reduced noise and reduced fuel consumption, but are sensitive to influences that can cause injector sticking.

The test is run with current injector design conforming to Euro V injector technology.

Full details of the CEC F-110-xx test method can be obtained from the CEC. The test cycle is summarised below.

1. Warm-Up stages:

| Step | Duration (minutes) | Engine Speed (rpm) | Torque (Nm) |
|---|---|---|---|
| 1 | 2 | 1000 | 10 |
| 2 | 3 | 2000 | 50 |
| 3 | 4 | 3500 | 75 |
| 4 | 3 | 3750 | 100 |

2. Main Run

| Step | Duration (seconds) | Engine Speed (rpm) | Torque (Nm) |
|---|---|---|---|
| 1 | 1470 | 1750 | 280 |
| 1 - Ramp → 2 | 270 | 3000 | — |
| 2 - Ramp → 1 | 30 | — | — |

The test procedure consists of alternating sequences of soak periods followed by cold starts preceding main run cycles of engine operation. There are 5 main runs and 6 cold starts.

If the engine should fail to start or stall during engine operation and cannot be restarted the test is aborted.

During the test ECU parameters are recorded together with exhaust temperatures to evaluate any indication of injector sticking. These parameters contribute to an overall demerit rating at the conclusion of the test.

The invention claimed is:

1. A fuel composition comprising as an additive one or more quaternary ammonium compounds of formula:

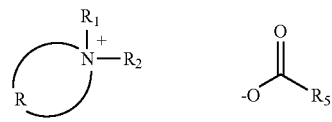

wherein each of R$^1$ and R$^2$ is independently selected from an optionally substituted alkyl, alkenyl or aryl group having less than 8 carbon atoms, R together with N forms an aliphatic or aromatic heterocycle having less than 12 carbon atoms and R$^5$ is hydrogen or an optionally substituted hydrocarbyl group; and a fuel.

2. The fuel composition according to claim 1 wherein the fuel is diesel fuel.

3. The fuel composition according to claim 2 which comprises one or more further detergents selected from the group consisting of:

an additional quaternary ammonium salt additive which is not a quaternary ammonium compound of formula:

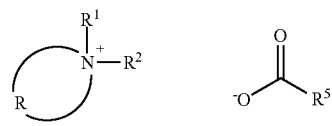

(i) wherein each of R$^1$ and R$^2$ is independently selected from an optionally substituted alkyl, alkenyl or aryl group having less than 8 carbon atoms, R together with N forms an aliphatic or aromatic heterocycle having less than 12 carbon atoms and R$^5$ is hydrogen or an optionally substituted hydrocarbyl group;

(ii) the product of a Mannich reaction between an aldehyde, an amine and an optionally substituted phenol;

(iii) the reaction product of a carboxylic acid-derived acylating agent and an amine;

(iv) the reaction product of a carboxylic acid-derived acylating agent and hydrazine;

(v) a salt formed by the reaction of a carboxylic acid with di-n-butylamine or tri-n-butylamine;

(vi) the reaction product of a hydrocarbyl-substituted dicarboxylic acid or anhydride and an amine compound or salt which product comprises at least one amino triazole group; and (vii) a substituted polyaromatic detergent additive.

4. The fuel composition according to claim 1 wherein the fuel is gasoline fuel.

5. The fuel composition according to claim 4 which comprises one or more gasoline detergents selected from the group consisting of:

(p) hydrocarbyl-substituted polyoxyalkylene amines or polyetheramines;

(q) acylated nitrogen compounds which are the reaction product of a carboxylic acid-derived acylating agent and an amine;

(r) hydrocarbyl-substituted amines wherein the hydrocarbyl substituent is substantially aliphatic and contains at least 8 carbon atoms;

(s) Mannich base additives comprising nitrogen-containing condensates of a phenol, aldehyde and primary or secondary amine;

(t) aromatic esters of a polyalkylphenoxyalkanol;
(u) an additional quaternary ammonium salt additive which is not a quaternary ammonium compound of claim 1; and
(v) tertiary hydrocarbyl amines having a maximum of 30 carbon atoms.

6. A quaternary ammonium salt of formula:

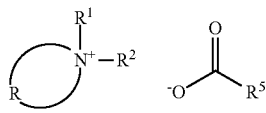

wherein each of $R^1$ and $R^2$ is independently selected from an optionally substituted alkyl, alkenyl or aryl group having less than 8 carbon atoms, R together with N forms an aliphatic or aromatic heterocycle having less than 12 carbon atoms and $R^5$ is hydrogen or an optionally substituted hydrocarbyl group.

7. The quaternary ammonium salt according to claim 6 which is prepared by reacting a cyclic tertiary amine of formula R=NR$^1$ with a quaternising agent selected from:
  (i) an ester of formula $R^5COOR^2$;
  (ii) a carbonate compound of formula $R^4OCOOR^2$ and then a carboxylic acid of formula $R^5COOH$; and
  (iii) an epoxide having less than 8 carbon atoms and a carboxylic acid of formula $R^5COOH$;
  wherein $R^4$ is an optionally substituted hydrocarbyl group.

8. The quaternary ammonium salt according to claim 7 wherein the quaternising agent is (ii) a carbonate compound of formula $R^4OCOOR^2$ and then a carboxylic acid of formula $R^5COOH$.

9. A quaternary ammonium salt which is the reaction product of:
  (a) a cyclic tertiary amine having less than 19 carbon atoms;
  (b) an epoxide having less than 8 carbon atoms; and
  (c) a carboxylic acid of formula $R^5COOH$; wherein $R^5$ is hydrogen or an optionally substituted hydrocarbyl group.

10. A method of preparing a quaternary ammonium salt, the method comprising reacting (a) a cyclic tertiary amine having less than 19 carbon atoms with (b) an epoxide in the presence of (c) a carboxylic acid of formula $R^5COOH$; wherein $R^5$ is hydrogen or an optionally substituted hydrocarbyl group.

11. The method according to claim 10 wherein component (a) comprises an amine of formula R=NR$^1$ in which $R^1$ is an optionally substituted hydrocarbyl group and R and N together form a heterocycle having less than 12 carbon atoms.

12. An additive composition comprising one or more quaternary ammonium compounds according to claim 6 and a diluent or carrier.

13. A lubricating composition comprising as an additive one or more quaternary ammonium compounds according to claim 6 and a lubricant.

14. A method of preparing a fuel composition according to claim 1, the method comprising adding the quaternary ammonium salt additive to the fuel after the fuel has left the distribution terminal.

15. A method of improving the performance of an engine, the method comprising combusting in said engine a fuel composition comprising as an additive one or more quaternary ammonium compounds according to claim 6.

16. The method according to claim 15 wherein the engine is a gasoline engine and the fuel is a gasoline fuel.

17. The method according to claim 15 wherein the engine is a diesel engine having a fuel injection system which comprises a high pressure fuel injection (HPFI) system with fuel pressures greater than 1350 bar.

18. The method according to claim 17 wherein improvement in performance is achieved by combating deposits in the engine.

19. The method according to claim 18 which combats internal diesel injector deposits.

20. The method according to claim 18 which combats external diesel injector deposits, including injector nozzle deposits and injector tip deposits.

21. The method according to claim 18 which combats fuel filter deposits.

22. The method according to claim 17 wherein the improvement in performance is a power gain compared to when combusting an unadditised base fuel and with clean injectors.

23. The method according to claim 15 to achieve "keep clean" performance.

24. The method according to claim 15 to achieve "clean up" performance.

25. The method according to claim 15 wherein the improvement in performance is achieved by combating deposits in the engine.

26. The method according to claim 15 wherein the improvement in performance is a power gain compared to when combusting an unadditized base fuel and with clean injectors.

* * * * *

UNITED STATES PATENT AND TRADEMARK OFFICE
CERTIFICATE OF CORRECTION

| | | |
|---|---|---|
| PATENT NO. | : 10,689,589 B2 | Page 1 of 1 |
| APPLICATION NO. | : 15/747950 | |
| DATED | : June 23, 2020 | |
| INVENTOR(S) | : Stephen Leonard Cook | |

It is certified that error appears in the above-identified patent and that said Letters Patent is hereby corrected as shown below:

In the Claims

In Column 36 of Claim 1, in the formula:
"$R_1, R_2$ and $R_5$"
Should read:
-- $R^1, R^2$ and $R^5$ --

Signed and Sealed this
Twentieth Day of October, 2020

Andrei Iancu
*Director of the United States Patent and Trademark Office*